(12) United States Patent
Lei et al.

(10) Patent No.: US 9,670,226 B2
(45) Date of Patent: Jun. 6, 2017

(54) SESQUITERPENOIDS

(71) Applicant: National Institute of Biological Sciences, Beijing, Beijing (CN)

(72) Inventors: Xiaoguang Lei, Beijing (CN); Sudan He, Beijing (CN); Chao Li, Beijing (CN); Ting Dong, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 0 days.

(21) Appl. No.: 15/333,079

(22) Filed: Oct. 24, 2016

(65) Prior Publication Data

US 2017/0044180 A1 Feb. 16, 2017

Related U.S. Application Data

(63) Continuation of application No. PCT/CN2015/077372, filed on Apr. 24, 2015, which is a continuation of application No. PCT/CN2014/076123, filed on Apr. 24, 2014.

(51) Int. Cl.

| | |
|---|---|
| *C07D 498/10* | (2006.01) |
| *C07D 493/10* | (2006.01) |
| *C07D 307/93* | (2006.01) |
| *A61K 31/343* | (2006.01) |
| *A61K 31/357* | (2006.01) |
| *A61K 31/4178* | (2006.01) |
| *A61K 31/4545* | (2006.01) |
| *A61K 31/496* | (2006.01) |
| *A61K 45/06* | (2006.01) |
| *C07D 493/20* | (2006.01) |

(52) U.S. Cl.
CPC .......... *C07D 493/10* (2013.01); *A61K 31/343* (2013.01); *A61K 31/357* (2013.01); *A61K 31/4178* (2013.01); *A61K 31/4545* (2013.01); *A61K 31/496* (2013.01); *A61K 45/06* (2013.01); *C07D 307/93* (2013.01); *C07D 493/20* (2013.01)

(58) Field of Classification Search
None
See application file for complete search history.

(56) References Cited

FOREIGN PATENT DOCUMENTS

CN 101318946 A 12/2008

OTHER PUBLICATIONS

OChemPal, http://www.ochempal.org/index.php/alphabetical/cd/cyclicketal/, accessed Feb. 28, 2017.*
Li Chao et al. A Biomimetic Total Synthesis of ( ± )-Ainsliadimer A. Letters. Sep. 2, 2010{Sep. 2, 2010), 19 (12): 4284-428L.
Macias, Francisco A et al. Dehydrozaluzanin C: a potent plant growth reg potential use as a natural herbicide template. Phytochemistry. 2000, 54(2): 165-171.

* cited by examiner

*Primary Examiner* — Noble Jarrell
(74) *Attorney, Agent, or Firm* — Richard Aron Osman

(57) ABSTRACT

The invention provides novel compounds and compositions for inhibiting IKKα/β, including treating disorders associated with IKKα/β activity, including cancer, autoimmune and inflammatory disorders, with a compound of structure:

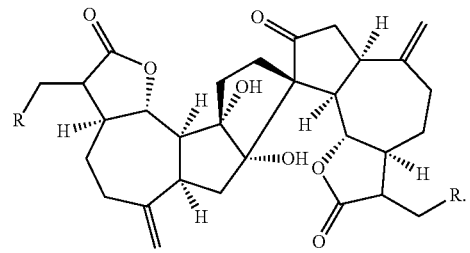

17 Claims, No Drawings

SESQUITERPENOIDS

This application is a continuation of PCT/CN2015/077372, filed: Apr. 24, 2015, which claims priority to PCT/CN2014/076123, filed: Apr. 24, 2014.

INTRODUCTION

The evolutionarily conserved nuclear factor-κB (NF-κB) signaling pathway plays key roles in inflammatory, immune responses and cell survival through regulating the transcription of numerous target genes[1-4]. The NF-κB family of transcription factors consists of five members, including p50, p52, p65 (RelA), c-Rel, and RelB, which form various dimeric complexes. The NF-κB dimers are normally sequestered in the cytoplasm by association with a member of the IκB inhibitory family (e.g. IκB α, IκBβ, IκBε) or the precursor proteins p100 and p105. NF-κB activation typically occurs by nuclear translocation of NF-κB dimers following inducible degradation of IκB or processing of precursor proteins in response to a variety of stimuli including cytokines like TNF-α or IL-1, growth factors, microbial infection and chemotherapeutic agents.

The canonical NF-κB activation depends on degradation of IκB, which is rapidly phosphorylated by active IκB kinase (IKK) complex, composed of two catalytic subunits, IKKα and IKKβ, and a regulatory subunit, IKKγ/NEMO (NF-κB essential modulator)[5]. IKKβ is the major subunit responsible for phosphorylation of IκB proteins. For example, IκB α is phosphorylated at Ser-32 and Ser-36[6], whereas IκBβ is phosphorylated at Ser-19 and Ser-23[7]. Phosphorylated IκB subsequently undergoes proteasome-mediated degradation, thereby liberating free NF-κB dimers to translocate to the nucleus and to promote gene transcription[8]. In addition, an alternative pathway designated as the non-canonical NF-κB relies on the inducible processing of p100[9]. This pathway mainly activates IKKα, which in turn phosphorylates p100 to trigger its proteolytic processing to p52, leading to nuclear translocation of p52 containing NF-κB dimer.

Aberrant activation of the NF-κB signaling pathway has been involved in a variety of human diseases including cancer, auto-immune diseases and chronic inflammatory diseases[2, 10, 11]. NF-κB pathway is important for cancer development and progression by regulating a wide variety of target genes involved in cell proliferation, cell survival, invasion, angiogenesis and metastasis[12]. Continuous activation of NF-κB is a common feature in the majority of human cancers, including both solid and hematopoietic malignancies[13]. Activated NF-κB triggers inducing expression of anti-apoptotic genes, including inhibitor of apoptosis protein (IAP) family[14], anti-apoptotic Bcl-2 family[15, 16] and cellular FLICE-inhibitory protein (cFILP)[17], which is associated with increased resistance of cancer cells to chemotherapy. Moreover, IKKβ has been recently shown to phosphorylate BAD and results in blocking BAD-mediated apoptosis[18]. In addition to its critical role in cancer, enhanced NF-κB activity is a hallmark of various autoimmune and inflammatory diseases. Chronic inflammatory condition has been shown to drive an increased cancer risk, such as colitis-associated colon cancer and hepatitis-associated liver cancer[19, 20]. Ample evidence suggests that inhibition of NF-κB activity represses cancer cell survival and tumor growth as well as inflammatory conditions. Therefore, the strategies focused on reducing NF-κB activity by specific small molecule inhibitors could offer significant therapeutic value for the treatment of these diseases.

Over the past decade, there has been a concerted effort to identify small molecule inhibitors of IKKβ due to its central role in canonical NF-κB pathway. Some small molecule inhibitors have been identified and exerted promising inhibitory effects in various experimental models of tumor and inflammatory diseases[12, 21]. However, there is as yet limited clinical experience of their efficacy and safety. Therefore, it is still of great importance that novel IKKα/β inhibitors with unique binding properties, high efficacy and low toxicity are identified to develop therapeutic agents suppressing both canonical and non-canonical NF-κB activation, and to uncover the mechanisms of IKK regulation of NF-κB signaling pathway.

Here we disclose a natural product (+)-ainsliadimer A (223) and synthetic derivatives tightly bind IKKα and IKKβ through the conserved cysteine residue 46, leading to the inactivation of both canonical and non-canonical NF-κB signaling pathway triggered by multiple stimuli. These are the first molecules to target functional Cys46 of IKKα/IKKβ and leads to their inactivation through a novel allosteric effect. Moreover, these molecules block LPS mediated inflammatory response and tumor growth in vivo. Our data indicate that (+)-ainsliadimer A and synthetic derivatives can function as potent inhibitors of IKKα/β, mediate NF-κB inhibition, anti-inflammatory and anti-cancer effects through selectively targeting the conserved cysteine of IKKα/β, and provide a useful drugs for treating cancer and inflammatory disorders.

SUMMARY OF THE INVENTION

The invention provides methods and compositions for inhibiting IKKα/β, including treating disorders associated with IKKα/β activity, including cancer, autoimmune and inflammatory disorders.

In an aspect the invention provides a compound of structure I, or salt thereof:

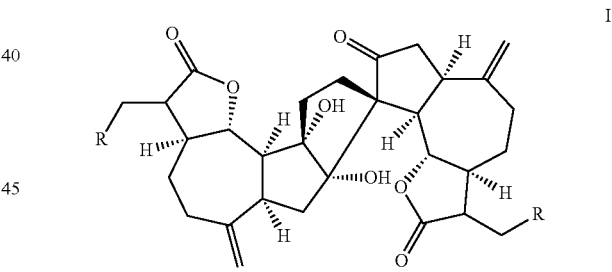

I wherein R is substituted or unsubstituted amine, hydroxyl, or thiol.

In another aspect the invention provides a compound of structure II, or salt thereof:

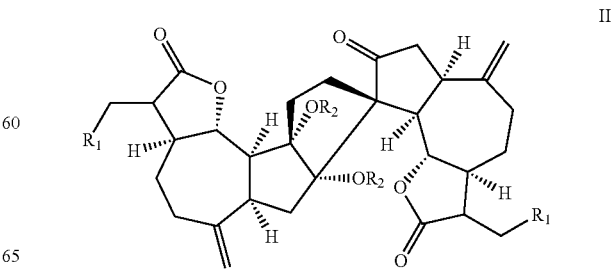

II wherein each R1 is independently substituted or unsubstituted amine, hydroxyl, or thiol; and each R2 is independently H or substituted or unsubstituted alkyl or acyl, or linked to the other R2 to form a cyclic ester or cyclic ether.

In embodiments:

R or R1 is alkyl or aryl-substituted, with 0-3 heteroatoms;

R or R1 is alkylthiol, arylthiol, alkyloxyl or aryloxyl;

R or R1 is benzenethiol or methoxyl;

R or R1 is alkylamine, dialykylaamine, arylamine, diarylamine, alkylarylamine, or cyclic amine;

R or R1 is dimethylamine, diethylamine, piperidine, pyrrolidine or morpholine;

R2 is H, C1-C8 alkyl, an acyl comprising a C1-C8 alkyl, or linked to the other R2 to form a C3-C9 cyclic ester or C4-C9 cyclic ether; and/or R2 is H, acetyl, methyl or each R2 is linked to the other R2 to form a dimethyl ketal.

In an aspect, the invention provides a pharmaceutical composition comprising a disclosed novel compound or salt thereof, particularly a pharmaceutically-acceptable salt, and a pharmaceutically-acceptable excipient, particularly in unit dosage.

In an aspect the invention provides a method of treating cancer comprising the step of administering to a person determined to be in need thereof a disclosed novel compound or compound of structure 223, or salt thereof:

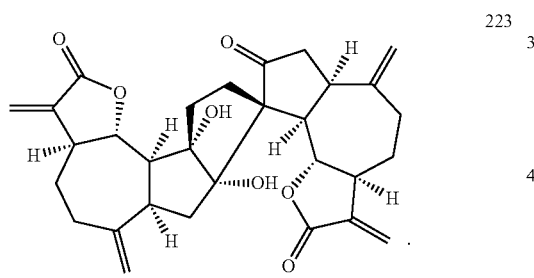

223

In an aspect the invention provides a method of treating an autoimmune or inflammatory disorder comprising the step of administering to a person determined to be in need thereof a disclosed novel compound, or salt thereof.

In embodiments, the therapeutic methods further comprise the subsequent step of determining a resultant therapeutic efficacy.

In an aspect the invention provides a pharmaceutical composition comprising components: (a) a disclosed novel compound or compound of structure 223, or salt thereof, and (b) a different anti-cancer medicament, which components may be copackaged or coformulated, and/or in unit dosage.

In an aspect, the invention provides a pharmaceutical composition comprising components: (a) a disclosed novel compound or salt thereof, and (b) a different anti-autoimmune or anti-inflammatory medicament, which components may be copackaged or coformulated, and/or in unit dosage.

In an aspect the invention provides a synthetic method useful for making a compound or compound of structure 223, the method comprising step (a) and/or step (b):

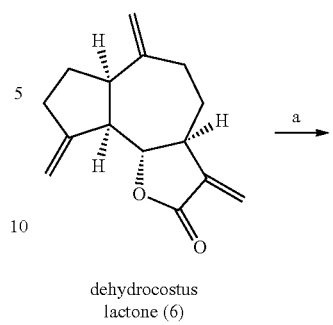

dehydrocostus lactone (6)

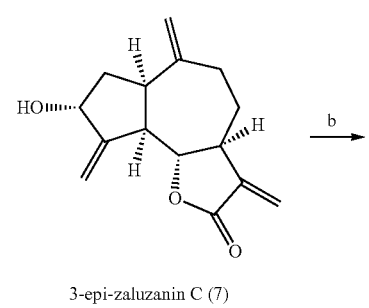

3-epi-zaluzanin C (7)

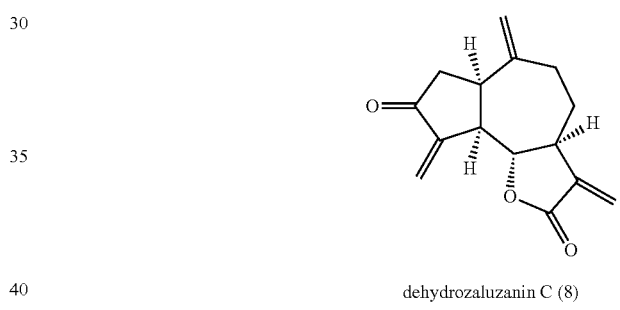

dehydrozaluzanin C (8)

wherein:

(a) dehydrocostus lactone 6 is reacted (typically in an organic solvent like $CH_2Cl_2$) with $SeO_2$ and t-BuOOH to form 3-epi-zaluzanin C 7; and (b) 3-epi-zaluzanin C 7 is reacted (typically in an organic solvent like $CH_2Cl_2$) with Dess-Martin periodinane to form dehydrozaluzanin C 8.

In embodiments the synthetic method further comprises subsequent steps (c), (d) and (e):

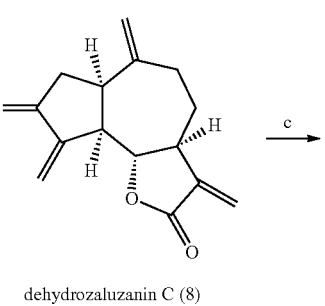

dehydrozaluzanin C (8)

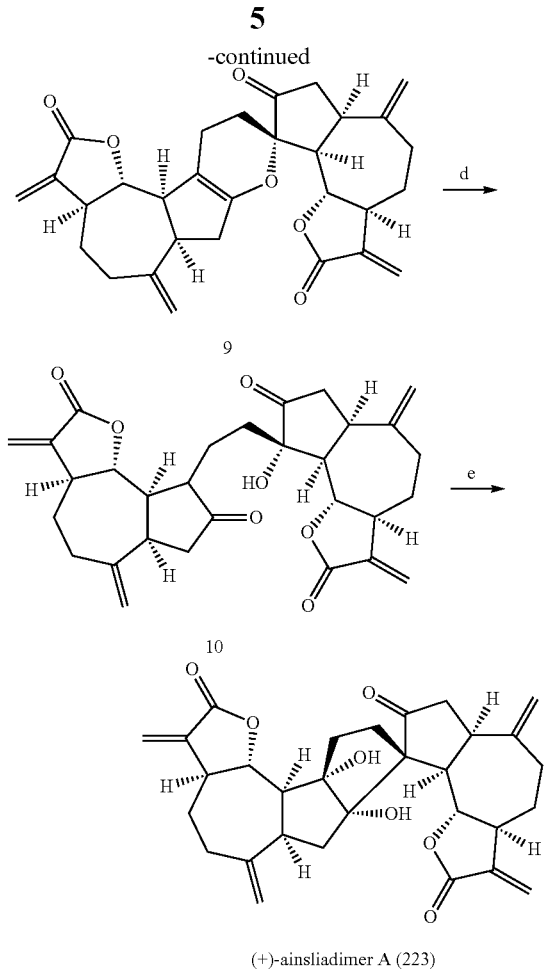

(+)-ainsliadimer A (223)

wherein:

(c) dehydrozaluzanin C 8 is reacted with a biphenol reagent (e.g. (+)-BIONOL (1,1'-Bi-2-naphthol) in EtOAc) to form dimer of dehydrozaluzanin C 9;

(d) dimer of dehydrozaluzanin C 9 is reacted with an acid (e.g HCL in THF/H$_2$O) to form diketone 10; and (e) diketone 10 is reacted with an organic base (e.g. triethylamine, diethylisopropylamine, or an amandine base, e.g. DBU (1,8-diazabicyclo[5.4.0]undec-7-ene) or DBN (1,5-diazabicyclo(4.3.0)non-5-ene), typically in an organic solvent) to form 223.

The invention encompasses all combination of the particular embodiments recited herein.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

In an aspect the invention provides a compound of structure I, or salt thereof, wherein R is substituted or unsubstituted amine, hydroxyl, or thiol.

Substituents are typically optionally-substituted, optionally heteroatom-containing organic moieties, typically hydrocarbon moieties, including alkyl, alkenyl, alkynyl and aryl moieties.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like. Preferred alkyls are C1-C24, C1-C12, C1-C8 or C1-C4.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof. Preferred alkenyls are C2-C24, C2-C12, C2-C8 or C2-C4.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof. Preferred alkynyls are C2-C24, C2-C12, C2-C8 or C2-C4.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH3)-CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene. Preferred aryls are C5-C24, C5-C18 or C5-C9.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are described herein.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR, —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR'—SO$_2$NR'", —NR"CO$_2$R', —NH—C(NH$_2$)=NH, —NR'C(NH$_2$)=NH, —NH—C(NH$_2$)=NR', —S(O)R', —SO$_2$NR'R", —NR"SO$_2$R, —CN and —NO$_2$, in a number ranging from zero to three, with those groups having zero, one or two substituents being particularly preferred. R', R" and R'" each independently refer to hydrogen, unsubstituted (C1-C8) alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —SiR'R"R'", —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO₂R', —CONR'R", —OC(O)NR'R", —NR"C(O)R', —NR"CO₂R', —NR'—SO₂NR"R'", —SO₂R', —SO₂NR'R", —NR"SO₂R, —CN and —NO₂.

Similarly, substituents for the aryl and heteroaryl groups are varied and selected from: halogen, —OR', —OC(O)R', —NR'R", —SR', —R', —CN, —NO₂, —CO₂R', —CONR'R", —C(O)R', —OC(O)NR'R", —NR"C(O)R', —NR"CO2R', —NR'—C(O)NR"R'", —NR'—SO₂NR"R'", —NH—C(NH2)=NH, —NR'C(NH₂)=NH, —NH—C(NH₂)=NR', —S(O)R', —SO₂R, —SO₂NR'R", —NR"SO₂R, —N₃, —CH(Ph)₂, perfluoro(C1-C4)alko-xy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR, —OC(O)R', —NR'R", —SR', —R, —CN, —NO₂, —CO₂R', —CONR'R", —C(O)R', —OC(O)NR'R", —NR"C(O)R', —S(O)R', —SO₂R', —SO₂NR'R", —NR"SO₂R, —N₃, —CH(Ph)₂, perfluoro(C1-C4)alkoxy and perfluoro(C1-C4)alkyl, where R' and R" are as defined above. Further preferred substituents are selected from: halogen, —OR', —OC(O)R', —NR'R", —R', —CN, —NO₂, —CO₂R', —CONR'R", —NR"C(O)R, —SO₂R, —SO₂NR'R", —NR"SO₂R, perfluoro(C1-C4) alkoxy and perfluoro(C1-C4)alkyl.

The substituent —CO₂H, as used herein, includes bio-isosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH₂)q-U—, wherein T and U are independently —NH—, —O—, —CH₂— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH₂—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)s-X—(CH₂)t-, where s and t are independently integers of from 0 to 3, and X is —O—, —NR'—, —S—, —S(O)—, —S(O)₂—, or —S(O)₂NR'—. The substituent R' in —NR'— and —S(O)₂NR'— is selected from hydrogen or unsubstituted (C1-C6)alkyl.

In particular embodiments applicable substituents are independently substituted or unsubstituted heteroatom, substituted or unsubstituted, optionally heteroatom C1-C6 alkyl, substituted or unsubstituted, optionally heteroatom C2-C6 alkenyl, substituted or unsubstituted, optionally heteroatom C2-C6 alkynyl, or substituted or unsubstituted, optionally heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or triflurom-ethyl ether (OCF3).

Exemplary active compound structures include:

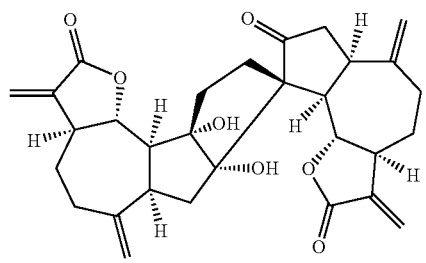

223

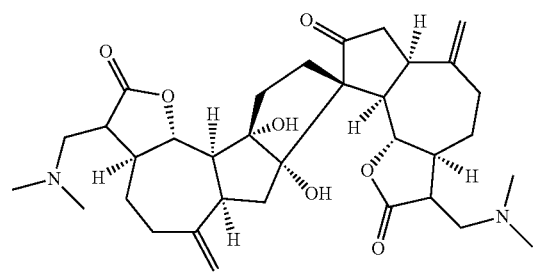

S1

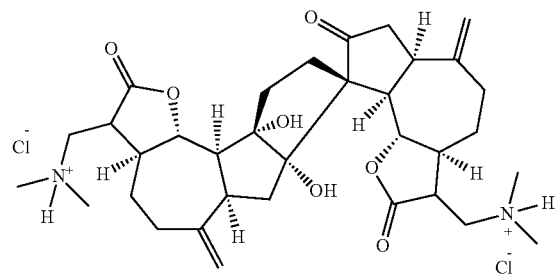

S2

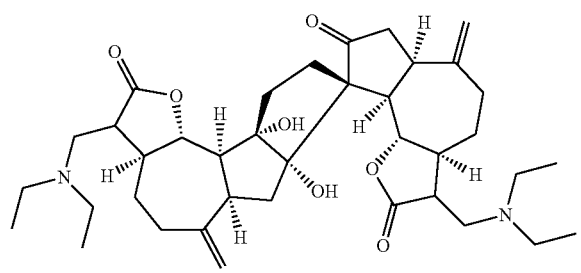

S3

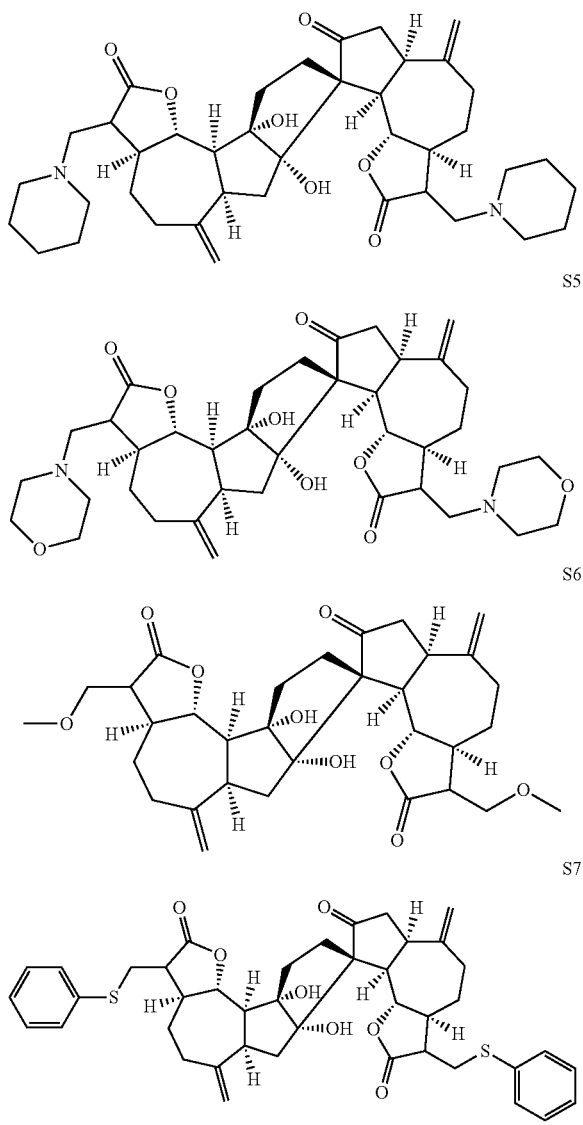

In an aspect, the invention provides a pharmaceutical composition comprising a disclosed novel compound or salt thereof, particularly a pharmaceutically-acceptable salt, and a pharmaceutically-acceptable excipient, particularly in unit dosage.

In an embodiment, the composition comprises components: a disclosed novel compound or salt thereof, and a different anti-autoimmune or anti-inflammatory medicament, which components may be copackaged or coformulated, and/or in unit dosage. In another embodiment, the composition comprises components: a disclosed novel compound or compound of structure 223, or salt thereof, and a different anti-cancer medicament, which components may be copackaged or coformulated, and/or in unit dosage.

In embodiments, the second medicament is for an autoimmune or inflammatory disorder, and preferably labeled or government (e.g. FDA) approved for such purpose; examples include acetylsalicyclate, ibuprofen, naproxen, prednisone, methotrexate, leflunomide, hydroxychloroquine sulfasalazine, azathioprine, cyclophosphamide, chloambucil, cyclosporine, gold salts, D-penicillamine, etanercept, infliximab, anakinra, adalimumab, rituximab, abatacept, golimumab, certolizumab pegol, tocilizumab, and tofacitinib.

In embodiments, the second medicament is for cancer (including tumors, neoplasias, malignancies, etc.), and preferably labeled or government (e.g. FDA) approved for such purpose; examples include Fluorouracil, Bevacizumab, Irinotecan Hydrochloride, Capecitabine, Cetuximab, Leucovorin Calcium, Oxaliplatin, Panitumumab, Regorafenib, and Ziv-Aflibercept.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because they may be easier to administer than the parent drug, may be more bioavailable by oral administration than the parent drug, and or may have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Some of the subject compounds possess asymmetric carbon atoms (optical centers) or double bonds; the racemates, diastereomers, geometric isomers and specifically designated or depicted chirality is preferred and in many cases critical for optimal activity; however all such isomers are all intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (2013). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The invention provides methods of treating disorders associated with IKKα/β activity, including cancer, autoimmune and inflammatory disorders. In an aspect the invention provides a method of treating cancer comprising the step of administering to a person determined to be in need thereof a disclosed novel compound or compound of structure 223, or salt or composition thereof. In an aspect the invention provides a method of treating an autoimmune or inflammatory disorder comprising the step of administering to a person determined to be in need thereof a disclosed novel compound, or salt or composition thereof. In embodiments, the therapeutic methods further comprise the subsequent step of determining a resultant therapeutic efficacy.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

The Natural Product (+)-Ainsliadimer A (223) Inhibits LPS Induced Inflammatory Cytokines In Vivo (+)-Ainsliadimer A (223) is a structurally unique and complex sesquiterpene lactone dimer with an unprecedented carbon skeleton, which was originally isolated from *Ainsliaea macrocephala* used in traditional Chinese medicine for the treatment of various diseases, including angina and rheumatoid arthritis[22]. Aiming for the systematical chemical genetic studies using bioactive natural products, we have successfully accomplished the first enantioselective total syntheses of 223 as well as other related dimeric and trimeric sesquiterpenoids[23-25], which provided us ample material to extensively investigate their biological activities and potential therapy application. 223 has been previously shown to exhibit inhibitory activity against the production of NO in a mouse macrophage cell line RAW264.7 stimulated by lipopolysaccharide (LPS)[22], a major cell wall component of Gram-negative bacteria. As an endotoxin, LPS is known to cause a systemic inflammatory response and acute tissue injury when injected into mice. Thus, we attempt to examine the effect of 223 on LPS-triggered inflammatory response in vivo. Mice were pre-injected with or without vehicle or 223, and then followed by administration of PBS or LPS. Serum inflammatory cytokines including TNF-α, IL-6 and IL-1β are highly induced in mice challenged with LPS compared to that from PBS-treated mice, while the up-regulation of these cytokines was greatly attenuated in mice pre-treated with 223 but not in vehicle pre-treated mice. These data show that 223 provides an anti-inflammatory agent in vivo.

223 Acts as a Potent Inhibitor of the NF-κB Pathway

The potent anti-inflammatory activity of 223 prompted us to investigate how it modulates pro-inflammatory cytokine responses. As a well-defined agonist of TLR4[12, 13], LPS specifically actives TLR4 and subsequently results in NF-κB activation and type I interferon (IFN) responses. We next evaluated the effect of 223 on LPS induced NF-κB activation. Phosphorylation of IκB is a key step in the activation of canonical NF-κB pathway. As expected, phosphorylated IκBα was detected in RAW264.7 cells after exposure to LPS for 10 or 20 minutes. Strikingly, pre-treatment of 223 could effectively block the phosphorylation of IκBα at the concentration of about 8 μM. In comparison with a well-known NF-κB inhibitor BMS-345541[26], 223 exhibited much stronger inhibitory effect against LPS-induced NF-κB activation. Meanwhile, we found that 223 had no effect on LPS-induced type I interferon (IFN) responses by assessing IFR3 phosphorylation, indicating that 223 specifically targets LPS trigged NF-κB signaling pathway. Furthermore, 223 markedly suppressed the phosphorylation of IκBα triggered by synthesized dsRNA poly(I:C), a TLR3 ligand[27]. These results implicate that 223 affects a common signaling component shared by TLR3- and TLR4-mediated NF-κB signaling. Besides TLRs, engagements of death receptors with corresponding ligands including TNF, also trigger NF-κB activation. We found 223 significantly inhibited TNF induced phosphorylation of IκBα in different cell lines. Taken together, these data establish that 223 acts as a potent inhibitor of the NF-κB pathway induced by diverse stimuli.

TNF receptor-associated factors (TRAFs) are important intermediates in NF-κB signaling pathway. For example, TRAF2 and TRAF5 regulate TNF-α receptor triggered IKK activation, whereas TRAF6 is required for IL-1 induced IKK activation[2]. The latter pathway can be reconstituted in cell-free extracts by adding recombinant TRAF6 protein. Phosphorylation of IKKα/β was detected in S100 cell lysates from 293T cells when incubated with recombinant TRAF6. Notably, the addition of 223 completely abolished TRAF6-induced phosphorylation of IKKα/β, indicating that (+)-ainsliadimer A disrupts the NF-κB pathway by intervening IKK complex or upstream activators.

Syntheses and Biological Evaluations of Chemical Probes Based on 223

To explore the functional target(s) of 223 associating with NF-κB pathway, we sought to prepare the chemical probes for affinity purification. Initial structure and activity relationship (SAR) studies enabled by total synthesis revealed that the hydroxyl analog 224 could fully retain the biological activity. In addition, the α, β-unsaturated enone moieties were shown to be essential for the biological activity as indicated by the inactive analog 225. We postulated that the enone moiety might be able to serve as a Michael acceptor to form a covalent bond with thiol functionality of the cysteine residue. Conceivably, the inactive analog 225 could be used to prepare a negative probe. Thus we synthesized both positive probe (Probe) and negative probe (NC) from 224 and 225 respectively with biotin and a tri(ethyleneglycol) linker. The biological evaluations of Probe and NC showed that the biotin-tagged positive probe retained the ability to effectively block NF-κB activation at 50 μM while the biotin-tagged negative probe completely lost the activity at the same concentration.

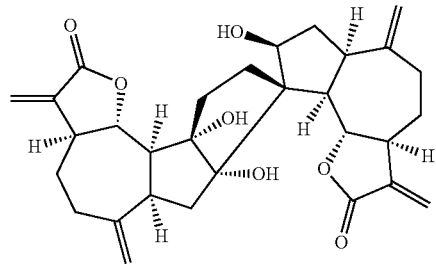

(224)

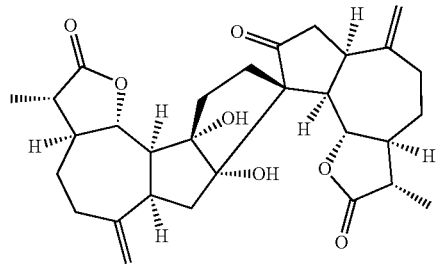

(225)

-continued (226)

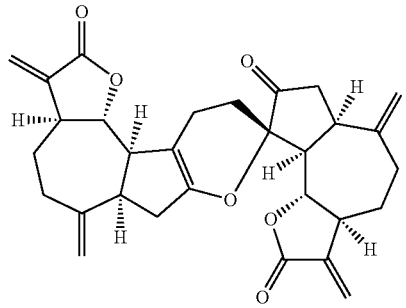

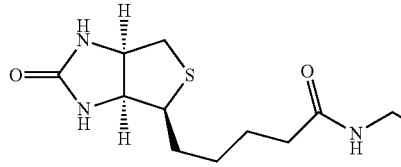

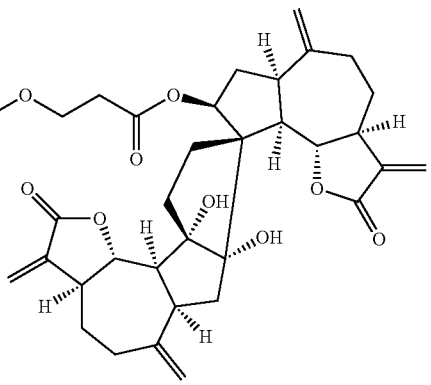

Positive chemical probe (Probe)

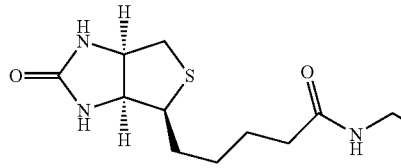

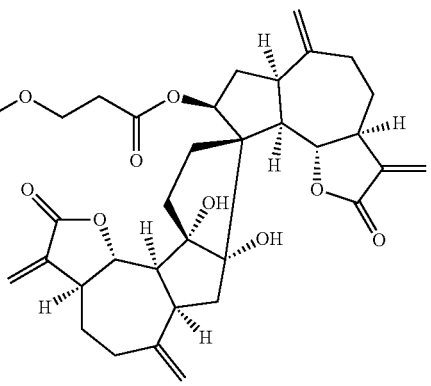

Negative chemical probe (NC)

223 Directly Targets IKKα and IKKβ.

To identify cellular proteins interacting with 223, we performed pull-down experiments using Probe and NC as the positive and negative probe, respectively. 293T cell lysates were incubated with streptavidin agarose beads which were pre-coupled with positive probe or negative probe. The proteins precipitated by streptavidin agarose beads were resolved by SDS-PAGE and stained with silver. Two clear bands observed at around 78 kDa and 80 kDa were specifically precipitated by the positive probe but not by the negative probe. Protein mass spectrometry analysis revealed that these two proteins are IKKα and IKKβ. We further monitored the presences of IKKα and IKKβ in the precipitates by immunoblotting. Consistently, both IKKα and IKKβ were specifically pulled down by the positive probe, but not by the negative probe. These data indicate that 223 targets IKKα and IKKβ, or a complex containing IKKα and IKKβ.

To determine whether 223 directly binds to IKKα and IKKβ, we generated recombinant IKKα and IKKβ proteins for further analysis. 293T cells were transfected with Flag-IKKα or Flag-IKKβ plasmid, and the recombinant Flag-IKKα or Flag-IKKβ was captured by anti-Flag agarose beads and was then eluted off the beads using Flag peptide. The purified Flag-IKKα or Flag-IKKβ was incubated with DMSO or increasing concentrations of Probe, and then the mixtures were resolved by SDS-PAGE, followed by immunoblotting with streptavidin or anti-Flag antibody. In the presence of Probe, a clear band with molecular weight of around 80 kDa was detected by streptavidin antibody and the signal intensity increased with increasing concentration of Probe, indicating a strong interaction between Probe and recombinant IKKα. Moreover, we also observed a similar interaction pattern between Probe and recombinant IKKβ, whereas this binding could be competed off by excess unlabeled 223 but not by 225. Notably, 223 had no association with IKKγ/NEMO, another subunit in IKK complex, as well as other molecular players in NF-κB pathway such as TAK1 and TAB1. Taken together, these data demonstrate that 223 could efficiently and specifically interact with IKKα and IKKβ, and the double bond is critical for its binding with IKKα and IKKβ.

Cys 46 of IKKα/β are Critical for their Bindings to 223

223 lost its inhibitory activity against NF-κB activation entirely when the enone moieties were saturated or in the presence of excess reducing agent dithiothreitol (DTT), indicating that the α, β-unsaturated moiety in 223 is a reactive Michael acceptor, which forms covalent bond with cysteine residues of its target proteins, resulting in inactivation of the targeting enzymes, as previously demonstrated by the natural products such as adenanthin[28]. We speculated that the conserved cysteine residues in IKKα and IKKβ might be the binding sites of 223. We blasted the sequences of IKKα and IKKβ and then we found nine conserved cysteine residues. In order to evaluate which of them is critical for the binding of 223, we individually mutated these nine cysteine residues of IKKβ into alanines. Among these mutants, C46A was the sole mutant that completely lost the ability to interaction with 223, while other eight mutants retained high affinity binding for 223 in a manner similar to wild-type IKKβ, indicating that Cys46 was essential for its binding to 223. As expected, mutation of Cys46 into serine in either IKKα or IKKβ abolished its corresponding interaction with 223.

To further clarify whether Cys46 is indeed the binding site of 223, we synthesized a peptide (#1), which encompasses amino acids 41-53 of human IKKβ. This peptide was tested for binding to 223 and probe by using MALDI-TOF (Matrix-Assisted Light Desorption/Ionization Time of Flight). m/z values at 2,047.978 and 2,479.259 were well matched with the calculated weights of #1+223 and #1+Probe, respectively. These results indicated that 223 and probe could bind with the IKKβ C46 containing peptide. As expected, the peptide #2 containing amino acids 41-53 of human IKKβ interacted with both 223 and probe. When cysteine 46 in #1 and #2 was replaced by either alanine or serine, called as peptides 1A, 2A, 1S and 2S respectively, these peptides lost the ability to bind either 223 or Probe. Moreover, the synthesized IKKβ C215 containing peptides #3 and #4, consisting of residues 202-220 and residues 212-231 respectively, showed no association with either 223 or Probe. In addition to the mutation binding assays supra, these results directly confirmed that 223 binds with IKKβ through cysteine 46.

Given that 223 covalently modifies IKKβ through Michael addition at C46. To verify the functional significance of this binding event, we performed in vitro kinase assays using WT-IKKβ or C46A IKKβ recombinant proteins as the kinase, and purified Flag-IκBα proteins as the substrate. As shown herein, both recombinant WT-IKKβ and C46A-IKKβ phosphorylated IκBα and the signal intensity of IκBα phosphorylation was similar, indicating that the replacement of Cys46 by alanine does not affect kinase activity of IKKβ. In the presence of 223, WT-IKKβ-induced phosphorylation of IκBα was significantly suppressed, whereas the phosphorylation of IκBα triggered by C46A-IKKβ was resistant to 223. Together, these results indicated that 223 inhibits IKKβ by direct modification of its C46 site.

223 is a Novel Allosteric Inhibitor of IKKα/β

To further explore how (+)-ainsliadimer A inactivates IKKα/β, we conducted the molecular dynamics (MD) simulations using the first crystal structure of IKKβ[29] to sample the conformational states of IKKβ upon 223 binding. According to the computational study, the binding mode shows that a stable hydrogen bond is forming between the backbone amide group of Cys46 and Michael acceptor carbonyl group of 223 during the simulation, stabilizing the transition state of Michael addition reaction. Additionally, 223 forms favorable hydrophobic interactions with residues including Trp58, Ile62, Val79, Leu91, Pro92 and Leu94, where an allosteric binding pocket had been identified in 3-phosphoinositide-dependent kinase 1 (PDK1)[30]. Moreover, mutation of Cys46 into Ala in IKKβ loses the capacity to induce auto-activation and downstream phosphorylation of IκBα. Collectively, these data indicate that Cys46 of IKKα/β acts as a novel allosteric site of these enzymes. We next asked whether 223 could directly affect IKKβ kinase activity. Notably, we observed that 223 showed extremely potent kinase inhibition effect against IKKβ with $IC_{50}$ of 76 nM comparing to the positive control pankinase inhibitor staurosporine ($IC_{50}$ 137 nM). In addition, 223 also represented excellent selectivity against a panel of structurally related kinases. These data indicate a model in which binding of 223 to Cys46 of IKKα/β triggers the conformational change of IKKα/β, leading to inactivation of these enzymes.

Since phosphorylation of p100 by IKKα is critical for NIK-mediated activation of the non-canonical NF-κB, we further investigated the effect of 223 on non-canonical NF-κB activation. Ectopic expression of NIK triggered the processing of p100 to p52, while addition of 223 prevented NIK-mediated production of p52, indicating that 223 blocks non-canonical NF-κB activation by disrupting IKKα activity.

223 Inhibits Growth of Cancer Cells and Xenograft Tumors.

In addition to its crucial role in control of the immune response, NF-κB pathway has been shown to negatively regulate apoptosis and positively regulates the onset and progression of tumor[12]. Aberrant or constitutive NF-κB activation has been observed in many cancer cells, which usually exert increased resistance to chemotherapy. Inhibition of NF-κB results in increased chemosensitivity of cancer cells to therapeutic drugs as well as cell death. To assess the effect of 223 on survival of cancer cells, we treated human cancer cells including cervical cancer HeLa cells, glioblastoma T98G cells and gastric adenocarcinoma BCG-823 cells with different concentration of 223. Dramatic cell death was observed in all of these cancer cells in response to 223. As expected, 223-triggered inhibition of cell survival was completely abolished by disruption of α,β-unsaturated moiety or addition of DTT. These data indicate that α,β-unsaturated moiety of 223 is essential for its biological activity of inhibiting NF-κB signaling and cell survival.

Next we further examined anti-tumor effect of 223 in vivo. Nude mice bearing a BGC-823 human gastric adenocarcinoma xenograft were treated with vehicle or 223 (25 mg/kg, qdx8) or 10-hydroxycamptothecin (HCPT), a widely used anti-tumor drug (30 mg/kg, q6dx2). Significant xenograft tumor remission was observed after 12 days in eight of eight mice treated with 223 compared to the vehicle-treated mice. Notably, 223 exerted a comparable anti-tumor effect to that of therapeutic drug HCPT. Importantly, the mice did not display any discernible side effects or significant changes in body weight during administration of 223 comparing with the significant body weight loss in the HCPT-treated group. Collectively, these data demonstrated inhibition of NF-κB by 223 resulted in significant death of human cancer cells and suppression of tumor growth with minimal undesired toxicities, implicating a novel IKK inhibitor for anticancer and anti-inflammatory therapeutics.

223 Analogs are Potent Inhibitors of the NF-κB Pathway, Block Phosphorylation of IκBα, and Inhibit Growth of Cancer Cells and Xenograft Tumors.

We designed and synthesized a panel of amine, hydroxyl, or thiol analogs of 223, including 1, 2, 3, 4, 5, 6, 7, and evaluated their effect on LPS induced NF-κB activation. Raw 264.7 cells were pre-incubated with 4 μM of analog or 223 for 2 h prior to stimulation with 20 ng/ml LPS. Cells were harvested after 20 minutes and total cell extracts were tested by western blot experiments for the occurrence of IκBα phosphorylation. 223 and analog pre-treatments effectively blocked the phosphorylation of IκBα. We also demonstrated that 223 and the analogs induce cell death in different cancer cells. In particular, (a) HeLa or (b) gastric adenocarcinoma BCG-823 cells were treated with DMSO, and analog or 223 for 48 hours and then the cell viability was determined by measuring ATP levels. Data show a dose response inhibition of cell survival for 223 and each tested analog. All experiments were repeated at least three times with similar results.

Synthetic Procedures; General Information:

$^1$H NMR spectra were recorded on a Varian 400 MHz spectrometer at ambient temperature with CDCl$_3$ as the solvent unless otherwise stated. $^{13}$C NMR spectra were recorded on a Varian 100 MHz spectrometer (with complete proton decoupling) at ambient temperature. Chemical shifts are reported in parts per million relative to chloroform ($^1$H, δ7.26; $^{13}$C, δ77.00). Data for $^1$H NMR are reported as follows: chemical shift, multiplicity (s=singlet, d=doublet, t=triplet, q=quartet, m=multiplet, br=broad), coupling constants and integration. Infrared spectra were recorded on a Thermo Fisher FT-IR200 spectrophotometer. High-resolution mass spectra were obtained at Peking University Mass Spectrometry Laboratory using a Bruker APEX Flash chromatography. Optical rotations were recorded on an AUTO-POL III digital polarimeter at 589 nm and are recorded as $[\alpha]_D^{20}$ (concentration in grams/100 mL solvent). Flash chromatography was performed using 200-400 mesh silica gel. Yields refer to chromatographically and spectroscopically pure materials, unless otherwise stated.

All reagents were used as supplied by Sigma-Aldrich, J&K and Alfa Aesar Chemicals. All reactions were carried out in oven-dried glassware under an argon atmosphere unless otherwise noted.

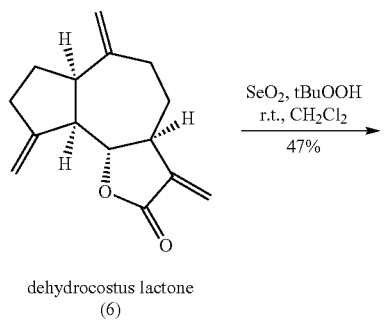

dehydrocostus lactone (6)

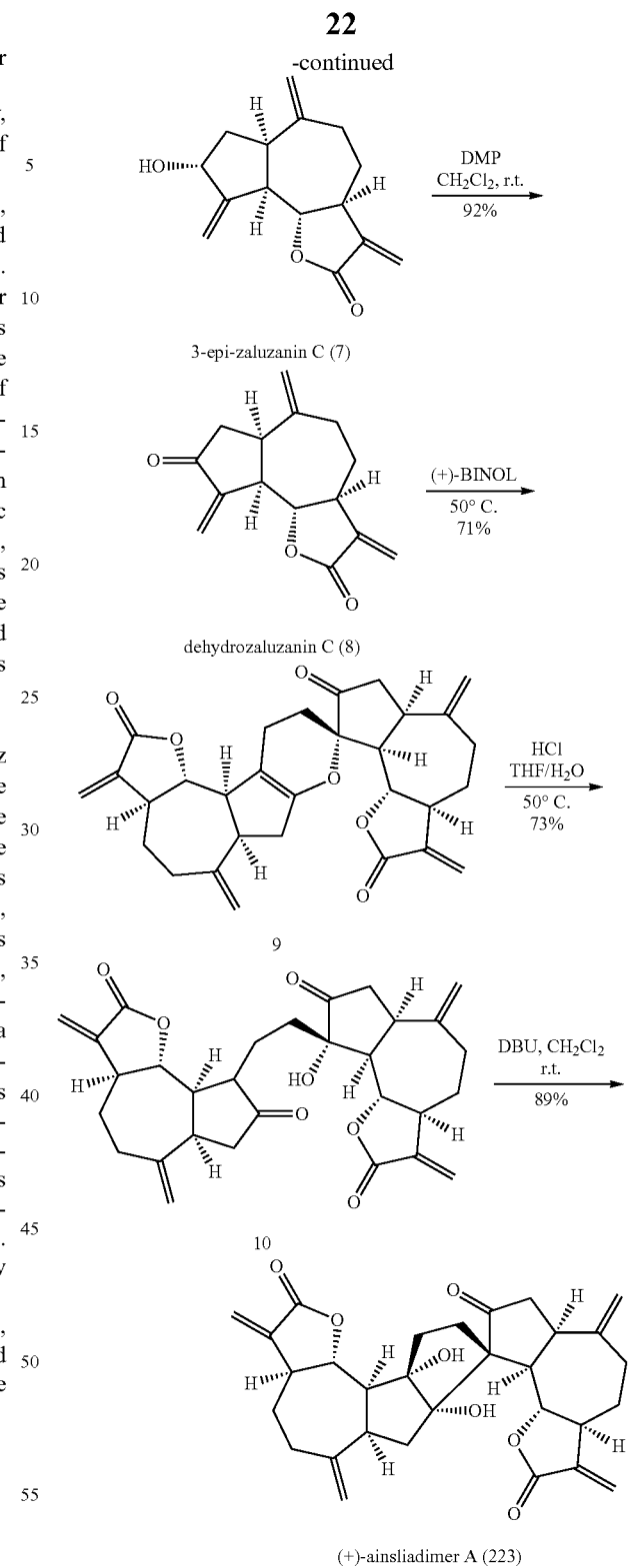

3-Epi-Zaluzanin C (7).

To a solution of dehydrocostus lactone (6, 11.7 g, 50.9 mmol) in CH$_2$Cl$_2$ (1.17 L) was added SeO$_2$ (2.82 g, 25.4 mmol) and t-BuOOH (5.5 M in H$_2$O, 101.7 mmol) with stirring. After 1 h, 30% Na$_2$S$_2$O$_3$ (500 mL) was added to the reaction mixture slowly. The organic layer was separated, the aqueous layer was further extracted by CH$_2$Cl$_2$ (500 mL×2). The combined organic layers were washed with brine, dried over Na$_2$SO$_4$ and concentrated in vacuo. The residue was purified by flash chromatography (PE:EtOAc=4:1) to afford 3-epi-zaluzanin C (7, 10.9 g, 47%) as a colorless solid. Spectroscopic data are in accordance with literature reported values (Ando, M. et al., Org. Chem. 1989, 54, 1952).

Dehydrozaluzanin C (8).

A solution of 3-epi-zaluzanin C (7, 10.9 g, 44.1 mmol) in CH$_2$Cl$_2$ (220 mL) was added to a solution of Dess-Martin periodinane (24.3 g, 57.3 mmol) in CH$_2$Cl$_2$ (220 mL) at 0° C. The reaction mixture was warmed to room temperature and stirred for 1 h. To the resulting mixture was added 30% aq. Na$_2$S$_2$O$_3$ (150 mL) and 10% aq. NaHCO$_3$ (150 mL). The resulting mixture was stirred at room temperature for 15 mm, the organic layer was separated, washed with water (500 mL) and brine (500 mL), the aqueous layers were further extracted by CH$_2$Cl$_2$ sequentially. The combined organic layer was then dried over Na$_2$SO$_4$, filter through silica gel, concentrated in vacuo to provide dehydrozaluzanin C (8, 9.60 g, 90%) as a light yellow solid. Spectroscopic data are in accordance with literature reported values (Bohlman, F; Le Van, N. Phytochemistry 1977, 16, 487).

Dimer of Dehydrozaluzanin C (9).

A solution of dehydrozaluzanin C (8, 63 mg, 0.26 mmol) and (+)-BINOL (37 mg, 0.13 mmol, 0.5 equiv) in EtOAc (5 mL) was concentrated in vacuo, and the resulting mixture was allowed to stand at 50° C. for 60 h. Purification by flash chromatography (PE:EtOAc=2:1) provided dimer of dehydrozaluzanin C (9, 45 mg, 71%) as a colorless oil, along with dehydrozaluzanin C (8, 10 mg, 14%). Spectroscopic data are in accordance with literature reported values (Li, C.; Yu, X.; Lei, X. Org. Lett. 2010, 12, 4284).

Diketone (10).

To a solution of dimer 9 (29 mg, 0.06 mmol) in THF (2 mL) was added 1N HCl (0.3 mL, 0.3 mmol), and the resulting mixture was stirred at 50° C. for 5 h. To the reaction mixture was slowly added sat. NaHCO$_3$ (2 mL), and the resulting mixture was extracted with EtOAc (10 mL). The aqueous layer was separated, and the organic layer was washed with brine, dried over Na$_2$SO$_4$, and concentrated in vacuo. Purification by flash chromatography (PE: EtOAc=1:4) provided 10 (22 mg, 73%) as a colorless oil. Spectroscopic data are in accordance with literature reported values.[Error! Bookmark not defined.]

(+)-Ainsliadimer A (223).

To a solution of compound 10 (10.5 mg, 0.021 mmol) in anhydrous CH$_2$Cl$_2$ (20 mL) was added a solution of DBU (38 μL, 0.25 mmol, 13 equiv) in anhydrous CH$_2$Cl$_2$ (5 mL). The resulting mixture was stirred at 20° C. for 15 h, before 0.05 M HCl (40 mL) was added. The organic layer was separated and washed with sat. NaHCO$_3$, brine, dried over Na$_2$SO$_4$, and concentrated in vacuo. Purification by flash chromatography (CHCl$_3$:MeOH=100:1) provided 223 (9.4 mg, 89%) as a colorless solid. Spectroscopic data are in accordance with literature reported values (Wu et al. Org. Lett. 2008, 10, 2397).

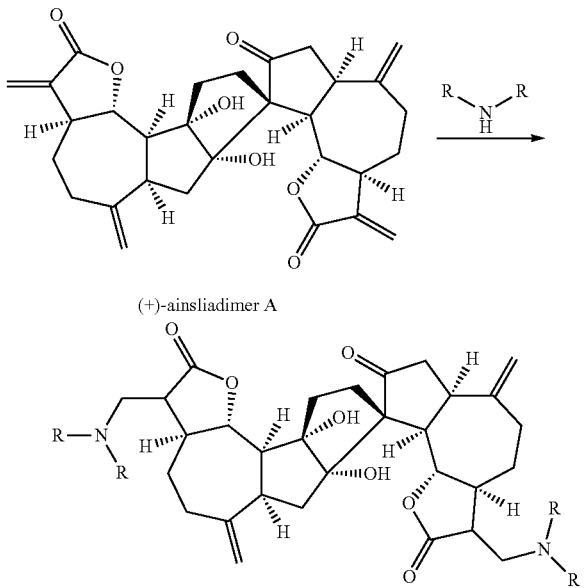

General Procedure:

To a solution of ainsliadimer A (0.032 mmol, 1 eq) in ethanol (1 mL) and CH$_2$Cl$_2$ (0.5 mL) was added dialkylamine (0.29 mmol, 9 eq) at 0° C., the reaction mixture was stirred at the same temperature and monitored by TLC till it was completed. The resulting mixture was concentrated directly give the desired product.

1: m.p. 102-103° C.; $[\alpha]^{22}{}_D$+98.5 (c 1.0, CH$_2$Cl$_2$); $^1$H NMR (400 MHz, CDCl$_3$) δ1.22-1.33 (m, 1H), 1.36-1.48 (m, 1H), 1.81-1.90 (m, 2H), 1.98-2.26 (m, 18H), 2.30-2.62 (m, 12H), 2.67-2.75 (m, 2H), 2.86-3.14 (m, 4H), 3.16 (s, br, 1H), 3.80 (s, br, 1H), 4.04 (dd, J=9.6 Hz, 11.2 Hz, 1H), 4.09 (t, J=8.8 Hz, 1H), 4.55 (s, 1H), 4.92 (s, 1H), 4.96 (s, 1H), 5.08 (s, 1H); $^{13}$C NMR (100 MHz, CDCl$_3$) δ26.2, 33.2, 33.4, 38.0, 38.2, 38.7, 39.3, 41.8, 44.8, 45.2, 45.2, 45.8, 45.8, 46.8, 50.4, 50.5, 53.0, 58.8, 58.9, 62.1, 82.7, 83.9, 89.3, 90.3, 112.8, 113.0, 148.2, 150.5, 176.4, 177.2, 225.1; IR (neat) ν$_{max}$ 1002, 1180, 1460, 1716, 1769, 2771, 2822, 2861, 2932, 3446 cm$^{-1}$; HRMS (ESI) [M+H$^+$] calculated for C$_{34}$H$_{49}$N$_2$O$_7$: 597.3534, found: 597.3537.

3: m.p. 100-101° C.; $[\alpha]^{23}{}_D$+80.0 (c 0.48, CHCl$_3$); $^1$H NMR (400 MHz, CDCl$_3$) δ0.83-0.89 (m, 2H), 0.95-1.02 (m, 12H), 1.22-1.42 (m, 2H), 1.78-1.91 (m, 2H), 1.99-2.74 (m, 24H), 2.83-2.98 (m, 4H), 3.03-3.16 (m, 3H), 3.78 (s, br, 1H), 4.03 (dd, J=10.0 Hz, 11.2 Hz, 1H), 4.07 (t, J=9.6 Hz, 1H), 4.56 (s, 1H), 4.91 (s, 1H), 4.96 (s, 1H), 5.08 (s, 1H); $^{13}$C NMR (100 MHz, CDCl$_3$) δ11.6, 11.8, 26.2, 38.3, 38.8, 41.8, 45.0, 45.5, 45.8, 46.9, 47.1, 51.0, 53.1, 53.1, 62.2, 82.7, 84.0, 89.3, 90.3, 112.7, 113.0, 148.4, 150.6, 176.7, 177.5, 225.1; IR (neat) ν$_{max}$ 773, 903, 1005, 1179, 1385, 1638, 1717, 1771, 2809, 2871, 2928, 2967, 3444 cm$^{-1}$; HRMS (ESI) [M+H$^+$] calculated for C$_{38}$H$_{57}$N$_2$O$_7$: 653.4160, found: 653.4148.

4: m.p. 115-116° C.; $[\alpha]^{24}{}_D$+100.6 (c 0.61, CHCl$_3$); $^1$H NMR (400 MHz, CDCl$_3$) δ0.83-0.89 (m, 2H), 1.21-1.60 (m, 12H), 1.81-1.90 (m, 2H), 1.98-2.60 (m, 26H), 2.73-2.78 (m, 2H), 2.86-2.97 (m, 2H), 3.03-3.11 (m, 3H), 3.79 (s, br, 1H), 4.02 (dd, J=9.6 Hz, 11.6 Hz, 1H), 4.07 (t, J=9.6 Hz, 1H), 4.55 (s, 1H), 4.91 (s, 1H), 4.96 (s, 1H), 5.07 (s, 1H); $^{13}$C NMR (100 MHz, CDCl$_3$) δ24.2, 24.2, 24.9, 25.9, 26.0, 26.2, 26.9, 33.2, 38.3, 38.8, 41.8, 44.6, 44.8, 45.4, 50.6, 51.0, 53.0, 54.8, 54.9, 58.7, 58.7, 62.1, 82.8, 83.9, 89.3, 90.4, 112.7, 112.9, 148.3, 150.6, 176.6, 177.4, 225.0; IR (neat) $v_{max}$ 991, 1005, 1178, 1456, 1637, 1717, 1771, 2778, 2852, 2931, 3431 cm$^{-1}$; HRMS (ESI) [M+H$^+$] calculated for $C_{40}H_{57}N_2O_7$: 677.4160, found: 677.4158.

5: m.p. 137-138° C.; $[\alpha]^{23}{}_D$+88.9 (c 0.68, CHCl$_3$); $^1$H NMR (400 MHz, CDCl$_3$) δ1.22-1.33 (m, 1H), 1.36-1.42 (m, 1H), 1.81-1.90 (m, 2H), 1.98-2.66 (m, 26H), 2.77-2.98 (m, 4H), 3.05-3.17 (m, 3H), 3.65-3.71 (m, 8H), 3.80 (s, br, 1H), 4.04 (dd, J=9.6 Hz, 11.2 Hz, 1H), 4.09 (t, J=10.4 Hz, 1H), 4.57 (s, 1H), 4.93 (s, 1H), 4.97 (s, 1H), 5.07 (s, 1H); $^{13}$C NMR (100 MHz, CDCl$_3$) δ 26.2, 33.2, 38.1, 38.1, 38.8, 41.8, 44.6, 45.4, 50.5, 50.7, 53.0, 54.0, 54.0, 58.0, 58.3, 62.1, 66.8, 82.7, 83.9, 89.3, 90.3, 112.8, 113.1, 148.2, 150.3, 176.1, 177.0, 224.9; IR (neat) $v_{max}$ 772, 1000, 1117, 1457, 1717, 1771, 2817, 2851, 2920, 3457 cm$^{-1}$; HRMS (ESI) [M+H$^+$] calculated for $C_{38}H_{52}N_2O_9$: 681.3746, found: 681.3741.

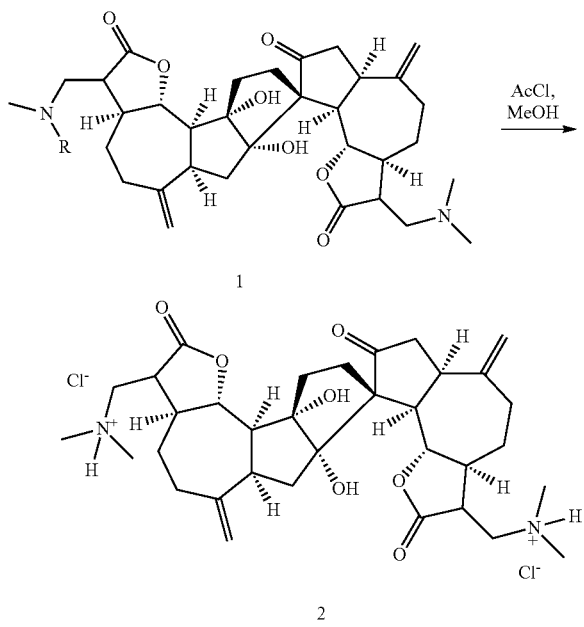

2: To MeOH (4 mL) was added acetyl chloride (150 μL), the resulting solution was stirred for 20 min before cooled to 0° C. To this cool solution was added dimethylamine-223 (36 mg, 0.06 mmol), and the resulting solution was stirred at 0° C. After 20 min, the reaction mixture was concentrated directly. The residue was dissolved in deionized water (10 mL), and washed with Et$_2$O (10 mL), the aqueous layer was concentrated to afford Dimethylamine-2HCl-223 (30 mg, 74%)

2: m.p. 152-153° C.; $[\alpha]^{22}{}_D$+25.6 (c 0.64, MeOH); $^1$H NMR (400 MHz, MeOH) δ1.38-1.48 (m, 1H), 1.55-1.65 (m, 1H), 1.87-1.92 (m, 2H), 2.03-2.39 (m, 9H), 2.46-2.68 (m, 6H), 2.86-3.22 (m, 18H), 3.37-3.47 (m, 2H), 3.54-3.65 (m, 2H), 4.60 (dd, J=9.6 Hz, 11.6 Hz, 1H), 4.51 (s, 1H), 4.56 (t, J=9.2 Hz, 1H), 5.00 (s, 1H), 5.05 (s, 1H), 5.07 (s, 1H); $^{13}$C NMR (100 MHz, CDCl$_3$) δ26.8, 32.1, 32.3, 33.8, 37.6, 38.6, 38.8, 39.0, 41.6, 42.3, 42.6, 42.7, 42.8, 44.3, 45.5, 45.6, 47.2, 49.0, 50.0, 52.2, 56.4, 56.7, 62.7, 85.5, 86.5, 90.3, 91.8, 112.9, 113.3, 149.6, 151.3, 178.2, 178.7, 228.6; IR (neat) $v_{max}$ 997, 1187, 1463, 1641, 1764, 2856, 2923, 3416 cm$^{-1}$; HRMS (ESI) [M-Cl$_2$] calculated for $C_{34}H_{50}N_2O_7$: 597.3525, found: 597.3538.

REFERENCES

1. Hayden, M. S. & Ghosh, S. Shared principles in NF-kappaB signaling. Cell 132, 344-362 (2008).
2. Vallabhapurapu, S. & Karin, M. Regulation and function of NF-kappaB transcription factors in the immune system. Annual review of immunology 27, 693-733 (2009).
3. Hoffmann, A. & Baltimore, D. Circuitry of nuclear factor kappaB signaling. Immunological reviews 210, 171-186 (2006).
4. Hayden, et al. Signaling to NF-kappaB. Genes & development 18, 2195-2224 (2004).
5. Hacker, H. & Karin, M. Regulation and function of IKK and IKK-related kinases. Science's STKE: signal transduction knowledge environment 2006, re13 (2006).
6. Brown, K., et al. Control of I kappa B-alpha proteolysis by site-specific, signal-induced phosphorylation. Science 267, 1485-1488 (1995).
7. DiDonato, J. et al. Mapping of the inducible IkappaB phosphorylation sites that signal its ubiquitination and degradation. Molecular and cellular biology 16, 1295-1304 (1996).
8. Karin, M. & Ben-Neriah, Y. Phosphorylation meets ubiquitination: the control of NF-[kappa]B activity. Annual review of immunology 18, 621-663 (2000).
9. Sun, S. C. Non-canonical NF-kappaB signaling pathway. Cell research 21, 71-85 (2011).
10. Ben-Neriah, Y. & Karin, M. Inflammation meets cancer, with NF-kappaB as the matchmaker. Nature immunology 12, 715-723 (2011).
11. Karin, M. Nuclear factor-kappaB in cancer development and progression. Nature 441, 431-436 (2006).
12. DiDonato, J. A., Mercurio, F. & Karin, M. NF-kappaB and the link between inflammation and cancer. Immunological reviews 246, 379-400 (2012).
13. Baud, V. & Karin, M. Is NF-kappaB a good target for cancer therapy? Hopes and pitfalls. Nature reviews. Drug discovery 8, 33-40 (2009).
14. Wang, C. Y., Mayo, M. W., Korneluk, R. G, Goeddel, D. V. & Baldwin, A. S., Jr. NF-kappaB antiapoptosis: induction of TRAF1 and TRAF2 and c-IAP1 and c-IAP2 to suppress caspase-8 activation. Science 281, 1680-1683 (1998).
15. Lee, H. H., Dadgostar, H., Cheng, Q., Shu, J. & Cheng, G. NF-kappaB-mediated up-regulation of Bcl-x and Bfl-1/A1 is required for CD40 survival signaling in B lymphocytes. Proceedings of the National Academy of Sciences USA 96, 9136-9141 (1999).
16. Tamatani, M. et al. Tumor necrosis factor induces Bcl-2 and Bcl-x expression through NFkappaB activation in primary hippocampal neurons. The Journal of biological chemistry 274, 8531-8538 (1999).
17. Thome, M. et al. Viral FLICE-inhibitory proteins (FLIPs) prevent apoptosis induced by death receptors. Nature 386, 517-521 (1997).
18. Yan, J. et al. Inactivation of BAD by IKK inhibits TNFalpha-induced apoptosis independently of NF-kappaB activation. Cell 152, 304-315 (2013).
19. Pikarsky, E. et al. NF-kappaB functions as a tumour promoter in inflammation-associated cancer. Nature 431, 461-466 (2004).
20. Greten, F. R. & Karin, M. The IKK/NF-kappaB activation pathway—a target for prevention and treatment of cancer. Cancer letters 206, 193-199 (2004).
21. Lee, D. F. & Hung, M. C. Advances in targeting IKK and IKK-related kinases for cancer therapy. Clinical cancer research: an official journal of the American Association for Cancer Research 14, 5656-5662 (2008). 22. Wu, Z. J. et al. Ainsliadimer A, a new sesquiterpene lactone dimer with an unusual carbon skeleton from *Ainsliaea macrocephala*. Organic letters 10, 2397-2400 (2008).
23. Li, C., Yu, X. & Lei, X. A biomimetic total synthesis of (+)-ainsliadimer A. Organic letters 12, 4284-4287 (2010).
24. Li, C., Dian, L., Zhang, W. & Lei, X. Biomimetic syntheses of (−)-gochnatiolides A-C and (−)-ainsliadimer B. Journal of the American Chemical Society 134, 12414-12417 (2012).
25. Li, C., Dong, T., Dian, L., Zhang, W. & Lei, X. Biomimetic syntheses and structural elucidation of the apoptosis-inducing sesquiterpenoid trimers: (−)-ainsliatrimers A and B. Chemical Science 4, 1163-1167 (2013).
26. Burke, J. R. et al. BMS-345541 is a highly selective inhibitor of I kappa B kinase that binds at an allosteric site of the enzyme and blocks NF-kappa B-dependent transcription in mice. The Journal of biological chemistry 278, 1450-1456 (2003).
27. Alexopoulou, L., Holt, A. C., Medzhitov, R. & Flavell, R. A. Recognition of double-stranded RNA and activation of NF-kappaB by Toll-like receptor 3. Nature 413, 732-738 (2001).
28. Liu, C. X. et al. Adenanthin targets peroxiredoxin I and II to induce differentiation of leukemic cells. Nature chemical biology 8, 486-493 (2012).
29. Xu, G et al. Crystal structure of inhibitor of κB kinase b. Nature 472, 325-330 (2011).
30. Sadowsky, J. D. et al. Turning a protein kinase on or off from a single allosteric site via disulfide trapping. Proceedings of the National Academy of Sciences of the USA 108, 6056-6061 (2011).
31. Berendsen, H. J., et al. GROMACS: A message-passing parallel molecular dynamics implementation. Computer Physics Communications 91, 43-56 (1995).
32. Hess, B., Kutzner, C., Van Der Spoel, D. & Lindahl, E. GROMACS 4: Algorithms for highly efficient, load-balanced, and scalable molecular simulation. Journal of chemical theory and computation 4, 435-447 (2008).
33. Case, D. et al. AMBER 12. University of California, San Francisco (2012).
34. Wang, J., et al. Automatic atom type and bond type perception in molecular mechanical calculations. Journal of molecular graphics and modelling 25, 247-260 (2006).
35. Wang, J., Wolf, R. M., Caldwell, J. W., Kollman, P. A. & Case, D. A. Development and testing of a general amber force field. Journal of computational chemistry 25, 1157-1174 (2004).

223 Derivatives are Potent Inhibitors of the NF-κB Pathway, Block Phosphorylation of IκBα, and Inhibit Growth of Cancer Cells and Xenograft Tumors.

We designed and synthesized a panel of amine, hydroxyl, or thiol derivatives of 223, and evaluated their effect of 223 on LPS induced NF-κB activation. As described above, raw 264.7 cells were pre-incubated with 4 μM of derivatives for 2 h prior to stimulation with 20 ng/ml LPS. Cells were harvested after 20 minutes and total cell extracts were tested by western blot experiments for the occurrence of IκBα phosphorylation. Derivative pre-treatments effectively blocked the phosphorylation of IκBα. We also demonstrated that the derivatives induce cell death in different cancer cells. In particular, (a) HeLa or (b) gastric adenocarcinoma BCG-823 cells were treated with DMSO, and derivative for 48 hours and then the cell viability was determined by measuring ATP levels. Data show a dose response inhibition of cell survival for each derivative tested.

Synthesis of Derivatives of (+)-Ainsliadimer A.

Reagents and conditions: a) different substituted amines, EtOH, r.t.; b) $CH_3COCl$, MeOH, 0° C.; $(CH_3)_2C(OCH_3)_2$, PPTS, benzene, 100° C.; d) $OsO_4$, NMO, acetone/water, 12 h; then $NaIO_4$, acetone/water.

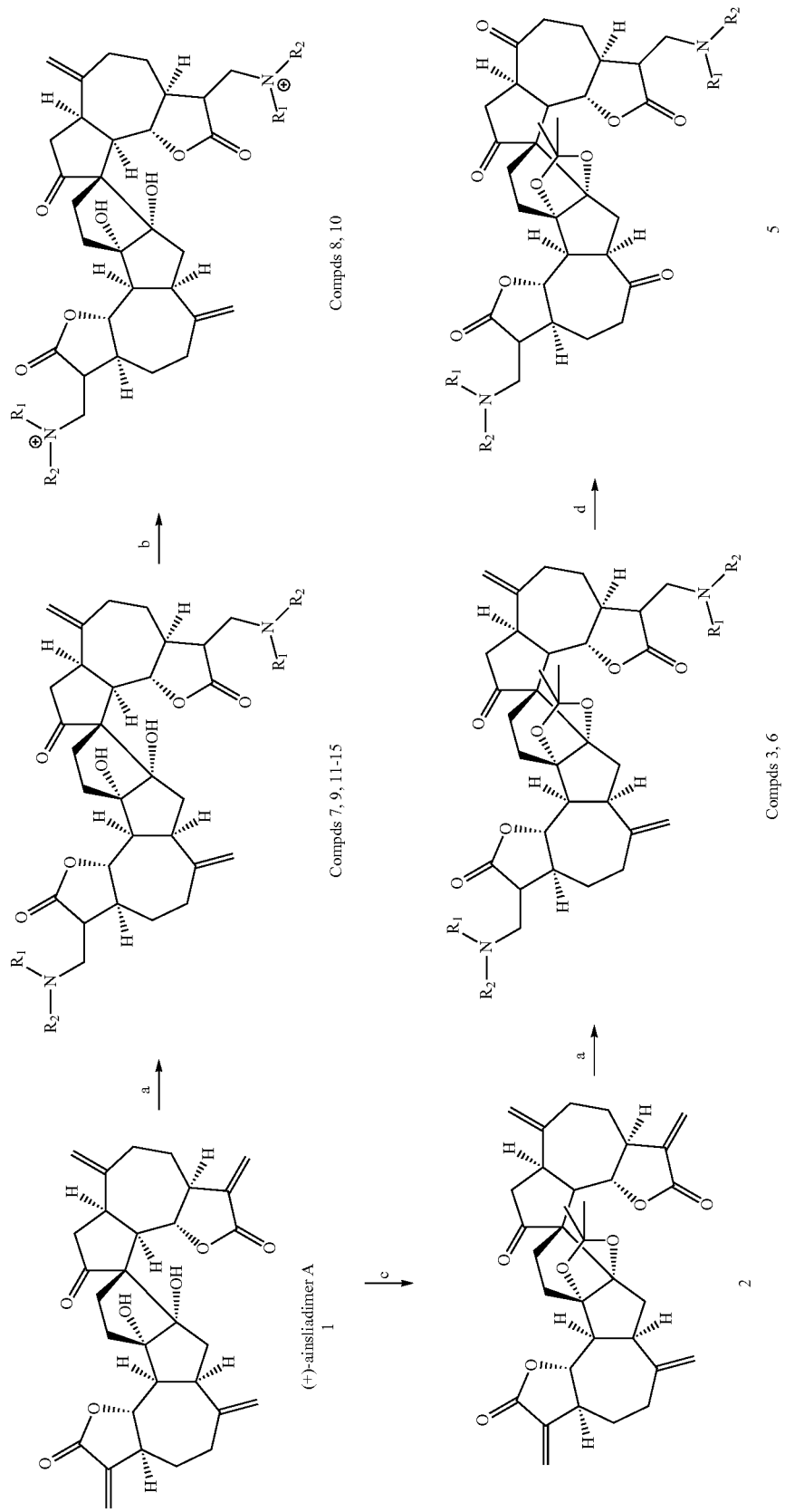

Synthetic Route for Ketals:

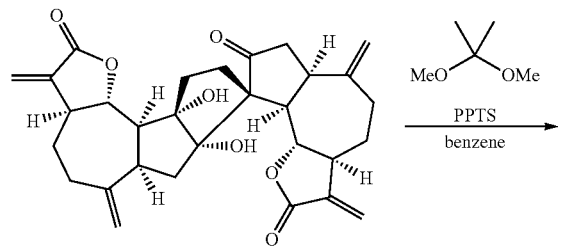

(+)-ainsliadimer A

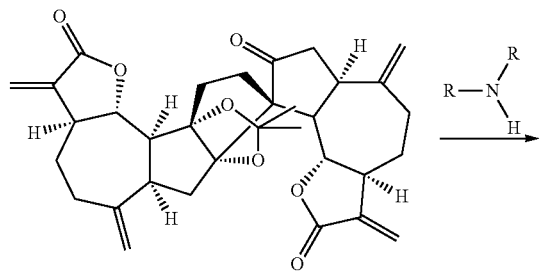

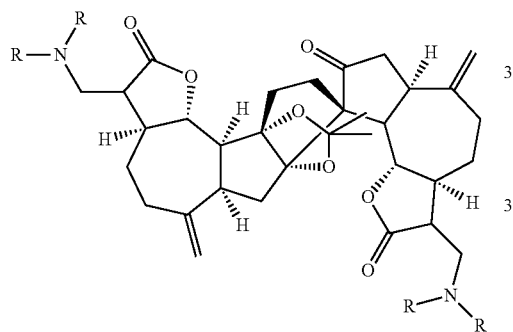

General Procedure for the Synthesis of Cyclic Ketals:

To a solution of ainsliadimer A in anhydrous benzene was added $(CH_3)_2C(OCH_3)_2$ and PPTS. Then the reaction was stirred at 100° C. for 14 h. After the reaction was finished, the benzene was removed, and the reaction mixture was extracted with DCM, washed with brine, dried over $Na_2SO_4$, concentrated in vacuo and purified by silica gel column to afford the desired ketals.

Representative Examples

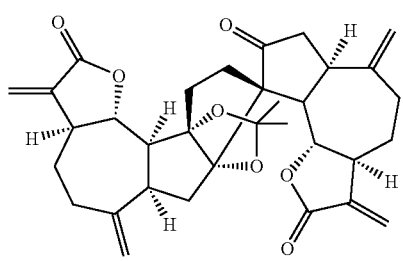

-continued

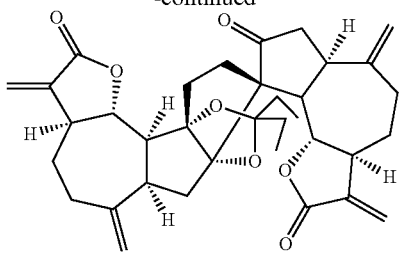

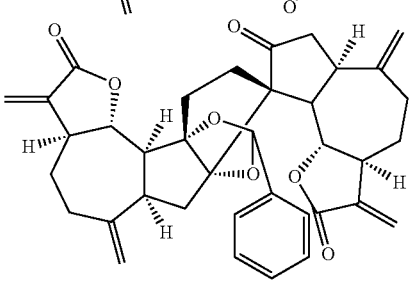

Synthetic Route for Esters:

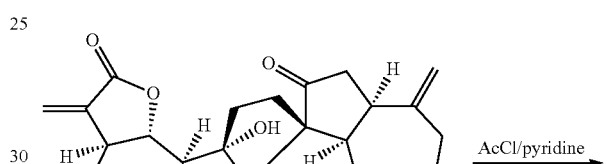

(+)-ainsliadimer A

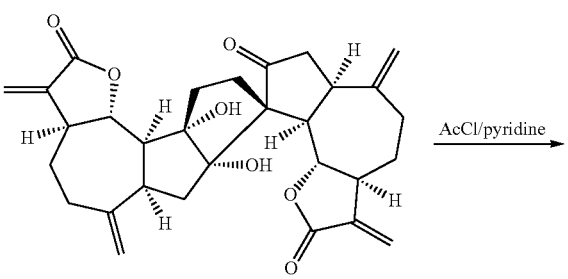

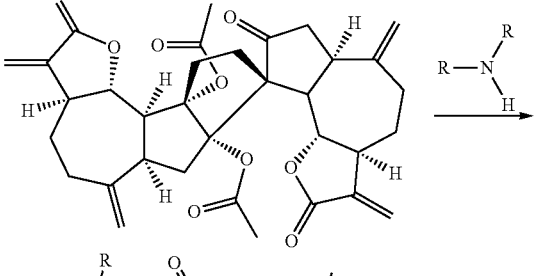

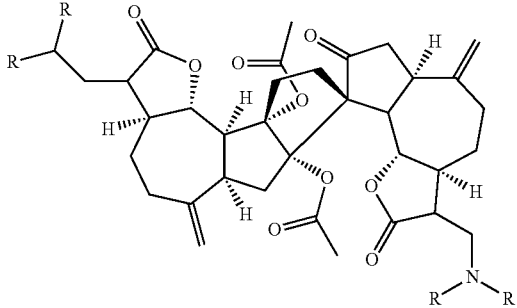

General Procedure for the Synthesis of Esters:

To a solution of ainsliadimer A in anhydrous pyridine was added AcCl. Then the reaction was stirred at rt for 24 h. After the reaction was finished, the pyridine was removed, and the reaction mixture was extracted with DCM, washed with brine, dried over $Na_2SO_4$, concentrated in vacuo and purified by silica gel column to afford the desired ester.

Representative Examples

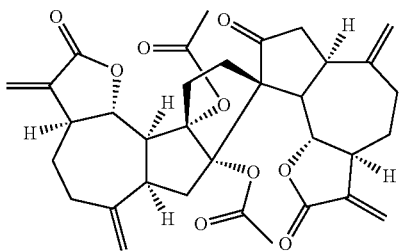

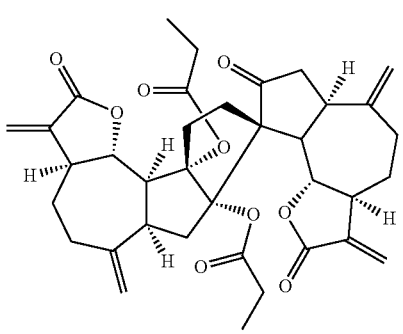

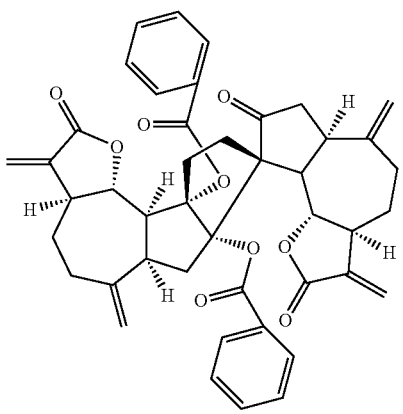

Synthetic Route for Ethers:

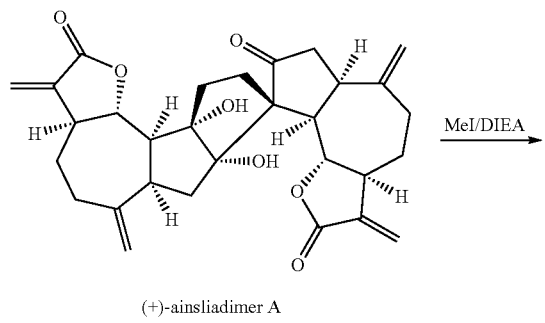

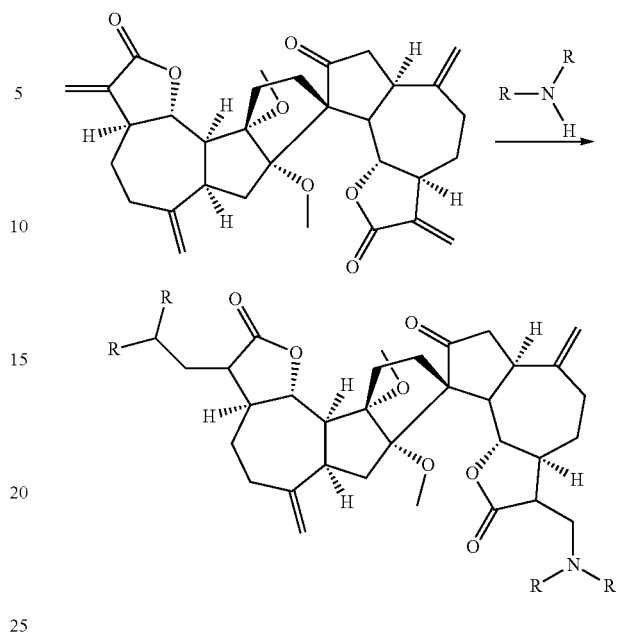

General Procedure for the Synthesis of Ethers:

To a solution of ainsliadimer A in anhydrous DCM was added MeI and DIEA. Then the reaction was stirred at 40° C. for 24 h. The reaction was quenched by adding sat. NH₄Cl aq. The reaction mixture was extracted with DCM, washed with brine, dried over Na₂SO₄, concentrated in vacuo and purified by silica gel column to afford the desired ether.

Representative Examples

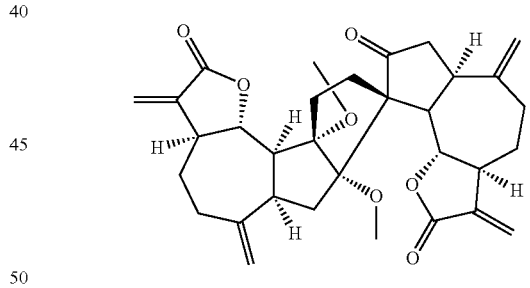

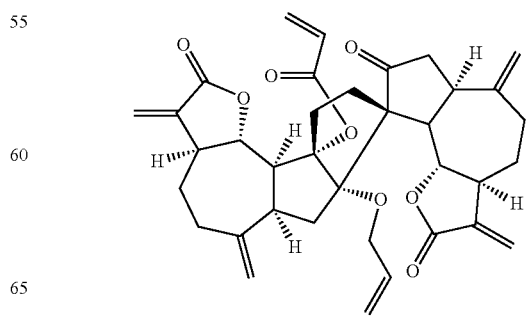

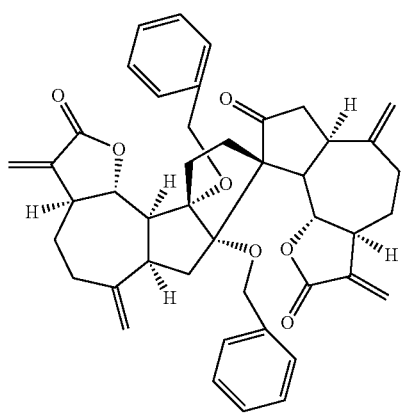
(+)-Ainsliadimer A Derivative Compounds
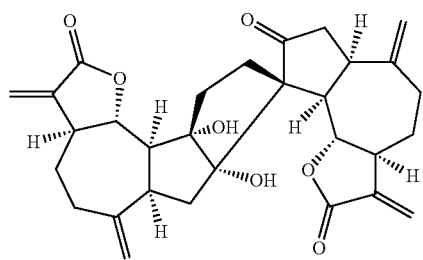
Ainsliadimer A
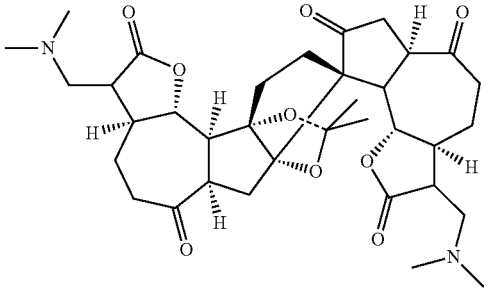
S10
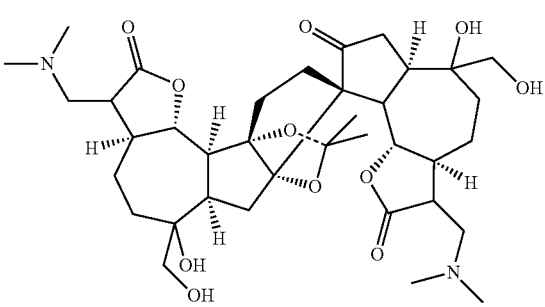
S11
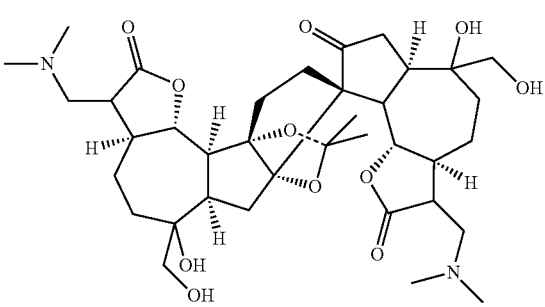
S6
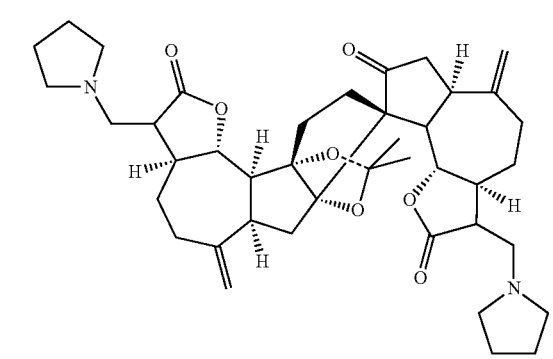
S7
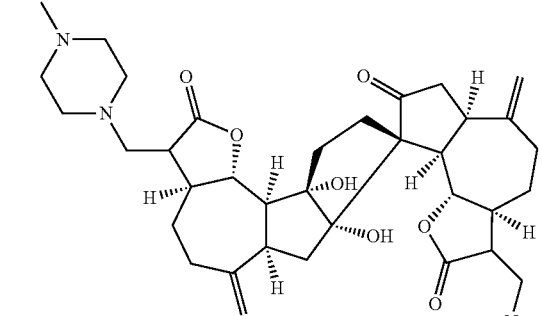
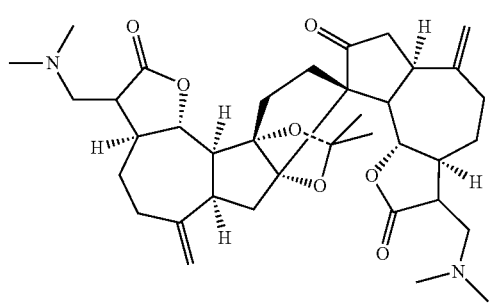
S8
S9

-continued
S8
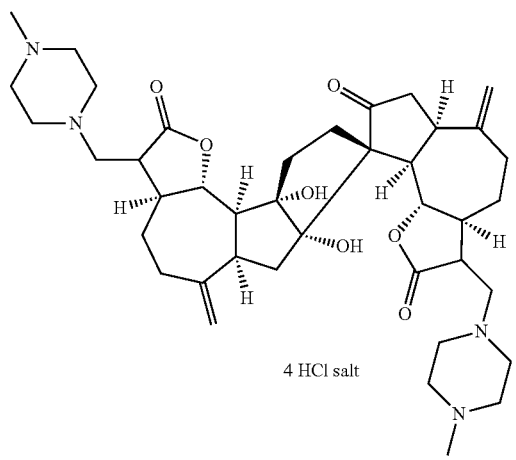
4 HCl salt
S15
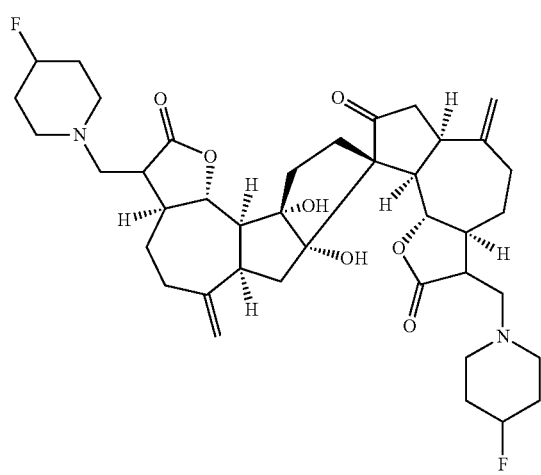
S16
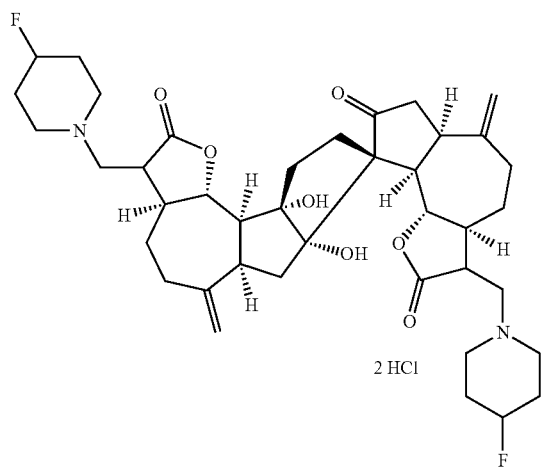
2 HCl
-continued
S17
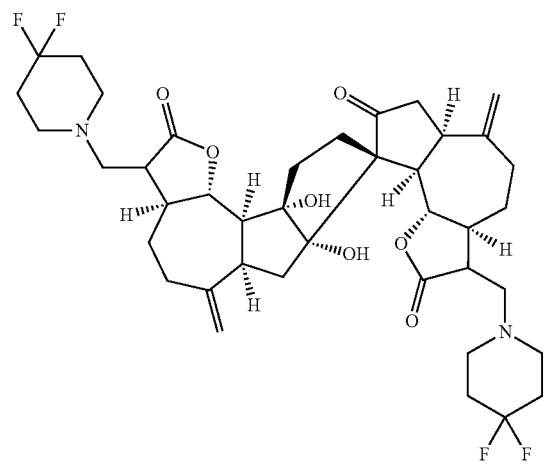
S18
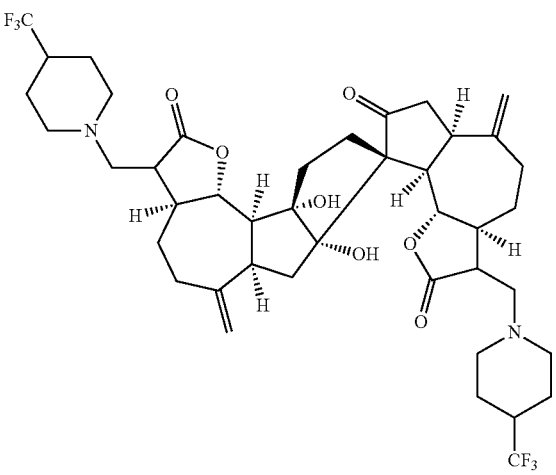
S19
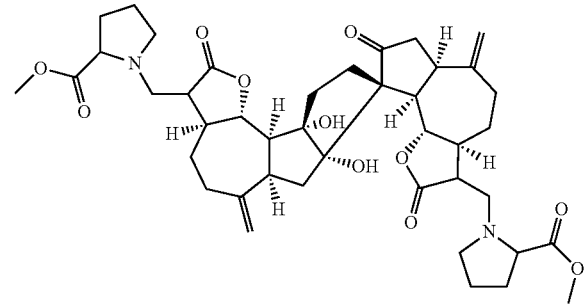

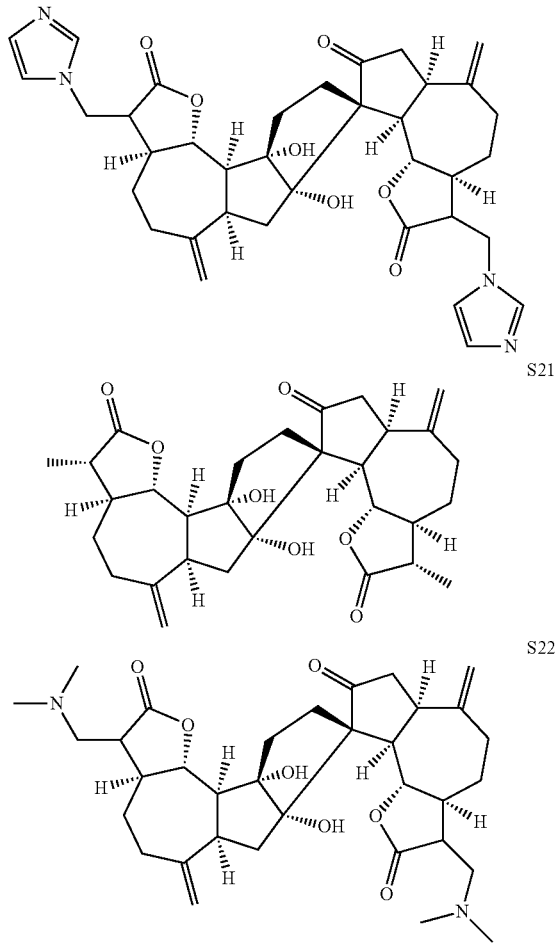

Derivatives of (+)-Ainsliadimer A Induce Cell Death in Cancer Cells.

Compounds 1-16 demonstrated dose response inhibition up to 95%; 17 was not significantly different from DMSO control.

Derivatives of (+)-Ainsliadimer A Inhibit IKKβ.

| Compound | 1 | 2 | 3 | 7 | 9 | 10 | 11 |
|---|---|---|---|---|---|---|---|
| IKKβ (IC$_{50}$, nM) | 75.68 | 56.05 | 41.75 | 50.63 | 39.79 | 23.48 | 42.87 |

Experimental Procedure; General Information:

$^1$H NMR spectra were recorded on a Bruker 400 MHz spectrometer at ambient temperature with CDCl$_3$ as the solvent unless otherwise stated. $^{13}$C NMR spectra were recorded on a Bruker 100 and 125 MHz spectrometer (with complete proton decoupling) at ambient temperature. Chemical shifts are reported in parts per million relative to chloroform ($^1$H, δ7.26; $^{13}$C, δ77.00). Data for $^1$HNMR are reported as follows: chemical shift, multiplicity (s=singlet, d=doublet, t=triplet, q=quartet, m=multiplet, br=broad), coupling constants and integration. Infrared spectra were recorded on a Thermo Fisher FT-IR200 spectrophotometer. High-resolution mass spectra were obtained at Peking University Mass Spectrometry Laboratory using a Bruker APEX Flash chromatography. Optical rotations were recorded on an AUTOPOL III digital polarimeter at 589 nm and are recorded as [α]$_D^{20}$ (concentration in grams/100 mL solvent). Flash chromatography was performed using 200-300 mesh silica gel. Yields refer to chromatographically and spectroscopically pure materials, unless otherwise stated.

Chemistry.

The synthesis of compounds A1-1 was conducted in a manner similar to the literature procedure (*Org. Lett.*, 2010, 12, 4284-4287). General procedure and characterization data for the representative compounds 2, 3, 7, 9, and 10 were listed below.

General Procedure:

Synthesis of compound 2. To a solution of (+)-Ainsliadimer A (50 mg, 0.0987 mmol, 1 eq) in benzene were added (CH$_3$)$_2$C(OCH$_3$)$_2$ (0.121 mL, 0.987 mmol, 10 eq) and PPTS (2.48 mg, 0.1 eq). Then the reaction was stirred at 100° C. for 14 h. After the reaction was finished, removed the benzene, extracted with DCM, washed with brine, dried with NaSO4, concentrated and purified by silica gel column (PE/EA 4/1) to obtain the target (35 mg, 65%). $^1$H NMR (400 MHz, CDCl$_3$): δ1.23-1.27 (m, 1H), 1.42 (s, 3H), 1.47 (s, 3H), 1.77-1.95 (m, 3H), 2.01-2.05 (m, 1H), 2.10-2.56 (m, 10H), 2.76-2.85 (m, 3H), 2.95-3.02 (m, 3H), 3.53-3.60 (m, 1H), 3.95-4.00 (m, 1H), 4.53-4.85 (dd, J$_1$=11.6 Hz, J$_2$=8.4 Hz, 1H), 4.86 (s, 1H), 4.87 (s, 1H), 4.93 (s, 1H), 5.02 (s, 1H), 5.46 (d, J=3.2 Hz, 1H), 5.58 (d, J=3.2 Hz, 1H), 6.17 (d, J=3.2 Hz, 1H), 6.25 (d, J=3.2 Hz, 1H).

Synthesis of compound 3. A mixture of dimethylamine hydrochloride (22 mg, 0.274 mmol, 10 eq) and DIPEA (48 μL, 0.274 mmol, 10 eq) in ethanol was stirred for 30 min at room temperature. Then compound 2 (15 mg, 0.027 mmol, 1 eq) was added, and the mixture was stirred for 10 h. after the reaction was finished, removed the solvent and purified by silica gel column (DCM:MeOH/10:1+0.1% NH$_3$—H$_2$O) to obtain the target (8 mg, 51%). $^1$H NMR (400 MHz, CDCl$_3$): δ1.25-1.36 (m, 3H), 1.42 (s, 3H), 1.47 (s, 3H), 1.69-1.91 (m, 3H), 2.04-2.19 (m, 4H), 2.24 (s, 6H), 2.27 (s, 6H), 2.29-2.54 (m, 11H), 2.60-2.72 (m, 3H), 2.76-2.82 (m, 1H), 2.86-2.90 (m, 1H), 2.96-3.02 (m, 1H), 3.50-3.57 (m, 1H), 3.95-4.00 (m, 1H), 4.46-4.51 (dd, J$_1$=11.2 Hz, J$_2$=8.8 Hz, 1H), 4.84 (s, 1H), 4.85 (s, 1H), 4.90 (s, 1H), 4.98 (d, J=1.6 Hz, 1H).

Synthesis of compound 7. The synthetic method was similar to synthesis of compound 3. $^1$H NMR (400 MHz, CDCl$_3$): δ1.20-1.30 (m, 2H), 1.36-1.45 (m, 1H), 1.81-1.90 (m, 2H), 1.99-2.28 (m, 7H), 2.29 (s, 3H), 2.30 (s, 3H), 2.33-2.68 (m, 25H), 2.78-2.84 (m, 2H), 2.87-2.98 (m, 2H), 3.03-3.18 (m, 3H), 3.80 (s, 1H), 4.01-4.11 (m, 2H), 4.56 (s, 1H), 4.92 (s, 1H), 4.97 (s, 1H), 5.08 (s, 1H).

Synthesis of compound 9. The synthetic method was similar to synthesis of compound 3. $^1$H NMR (400 MHz, CDCl$_3$): δ1.22-1.64 (m, 3H), 1.81-1.94 (m, 10H), 1.99-2.23 (m, 5H), 2.27-2.48 (m, 12H), 2.50-2.67 (m, 8H), 2.76-2.83 (m, 2H), 2.87-2.98 (m, 2H), 3.01-3.19 (m, 3H), 3.81 (s, 1H), 4.01-4.11 (m, 2H), 4.57 (s, 1H), 4.58-4.63 (br, 1H), 4.68-4.76 (br, 1H), 4.92 (s, 1H), 4.97 (s, 1H), 5.08 (s, 1H).

Synthesis of compound 10. To MeOH (2 mL) was added acetyl chloride (10 μL), the resulting solution was stirred for 20 min before cooled to 0° C. To this cool solution was added compound 9 (11 mg, 0.02 mmol), and the resulting solution was stirred at 0° C. After 20 min, the reaction mixture was concentrated directly. The residue was dissolved in deionized water (3 mL), and washed with Et$_2$O (10 mL), the aqueous layer was concentrated to afford 2HCl salt. 1H NMR (400 MHz, CD3OD): δ1.24-1.59 (m, 3H), 1.83-1.93 (m, 2H), 1.99-2.40 (m, 19H), 2.49-2.66 (m, 4H), 2.88-2.95 (m, 1H), 3.07-3.22 (m, 5H), 3.34-3.50 (m, 7H), 3.57-3.69 (m, 5H), 4.26-4.40 (m, 2H), 4.55 (s, 1H), 4.94-4.96 (br, 3H), 5.06 (s, 1H), 5.13 (s, 1H).

What is claimed is:

1. A compound of structure II, or salt thereof:

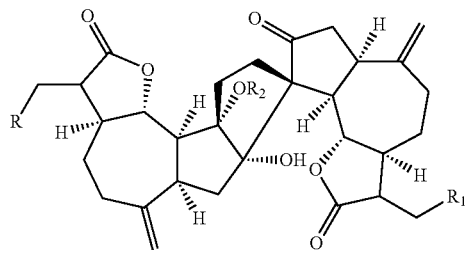

wherein:
each R1 is independently substituted or unsubstituted amine, hydroxyl, or thiol; and
each R2 is independently H or substituted or unsubstituted alkyl or acyl, or linked to the other R2 to form a cyclic ester or cyclic ether.

2. The compound of claim 1 wherein R1 is alkyl or aryl-substituted, with 0-3 heteroatoms, or salt thereof.

3. The compound of claim 1 wherein R1 is alkylthiol, arylthiol, alkyloxyl or aryloxyl, or salt thereof.

4. The compound of claim 1 wherein R1 is benzenethiol or methoxyl, or salt thereof.

5. The compound of claim 1 wherein R1 is alkylamine, dialykylaamine, arylamine, diarylamine, alkylarylamine, or cyclic amine, or salt thereof.

6. The compound of claim 1 wherein R1 is dimethylamine, diethylamine, piperidine, pyrrolidine or morpholine, or salt thereof.

7. The compound of claim 1 wherein R2 is H, C1-C8 alkyl, an acyl comprising a C1-C8 alkyl, or linked to the other R2 to form a C3-C9 cyclic ester or C4-C9 cyclic ether, or salt thereof.

8. The compound of claim 1 wherein R2 is H, acetyl, methyl or each R2 is linked to the other R2 to form a dimethyl ketal, or salt thereof.

9. The compound of claim 1 of a following structure, or salt thereof:

S1
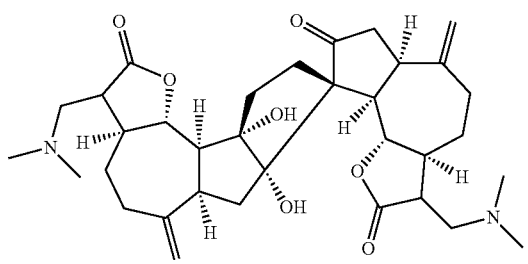

S2
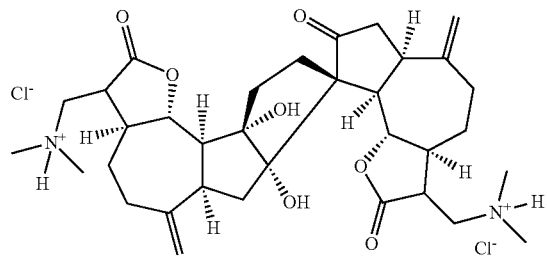

S3
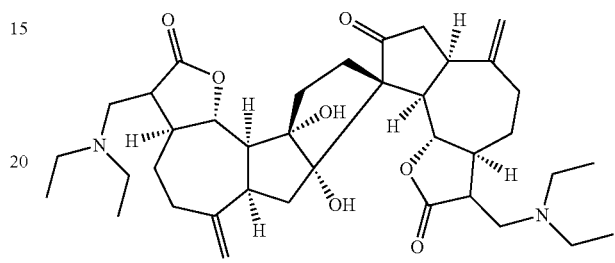

S4
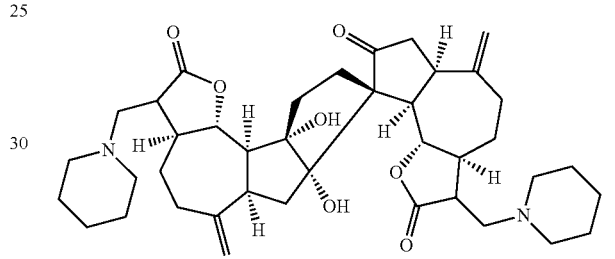

S5
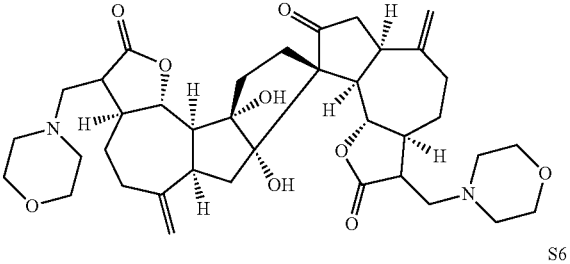

S6
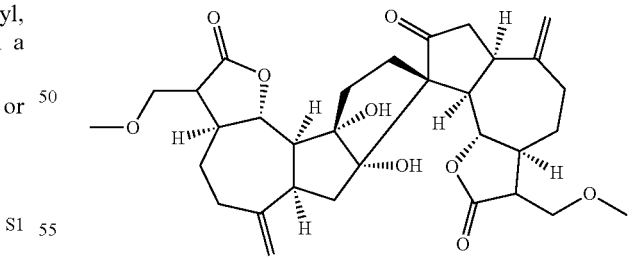

S7
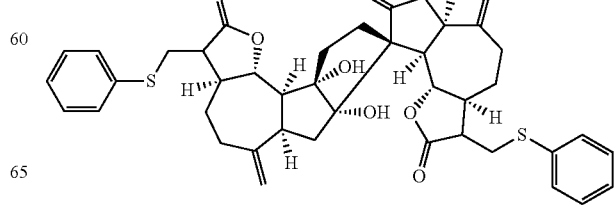

S9
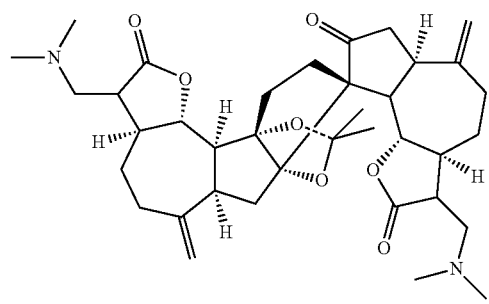
S12
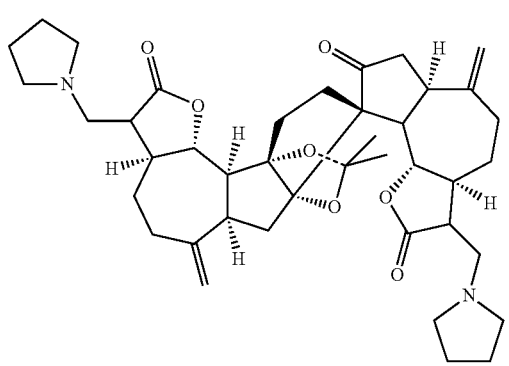
S13
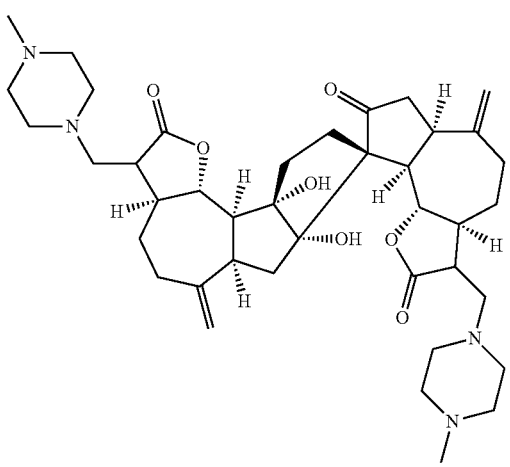
S14
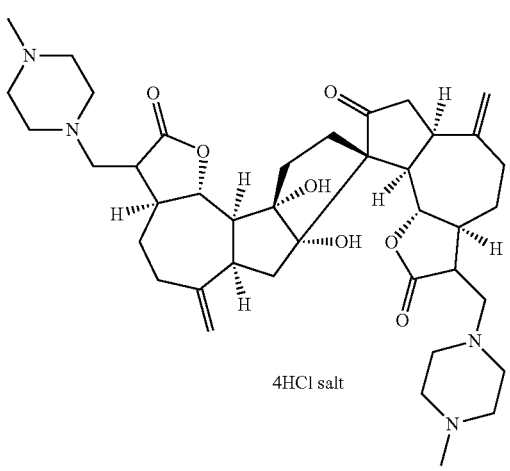
4HCl salt
S15
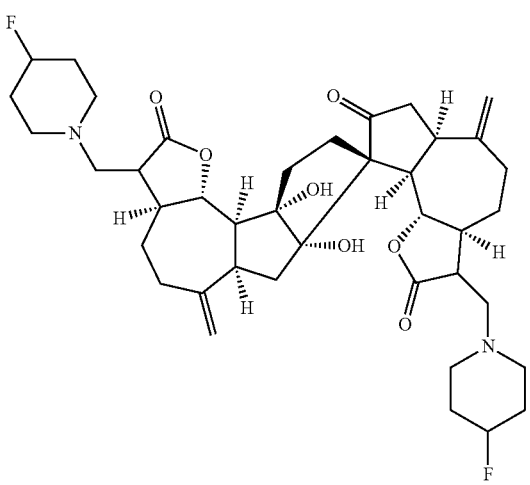
S16
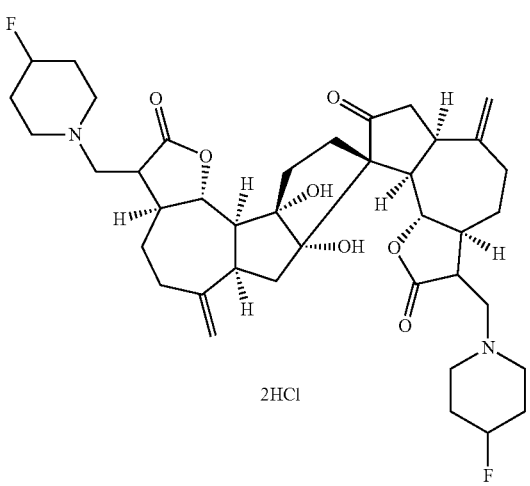
2HCl
S17
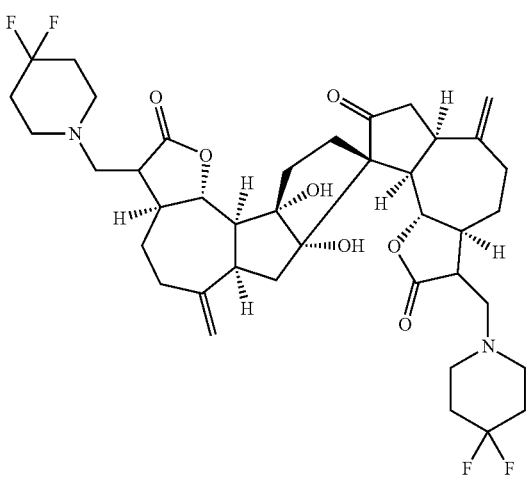

-continued

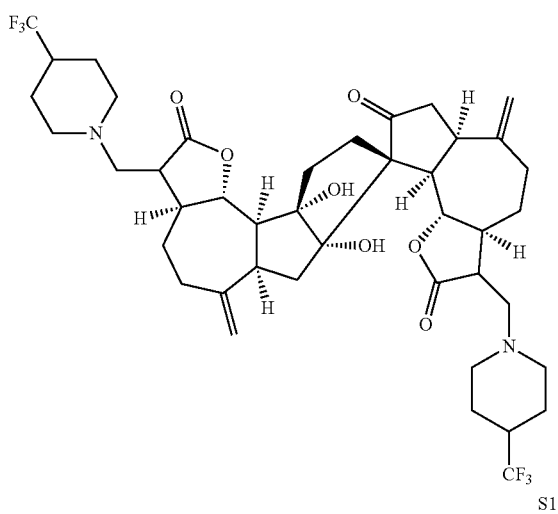

S18

S19

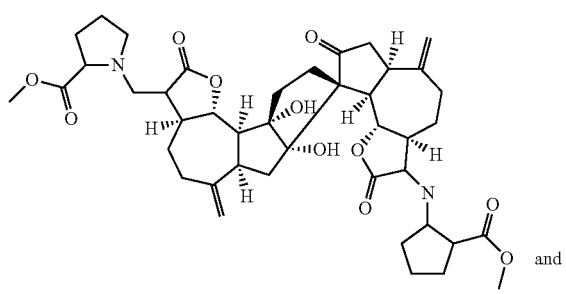

S20

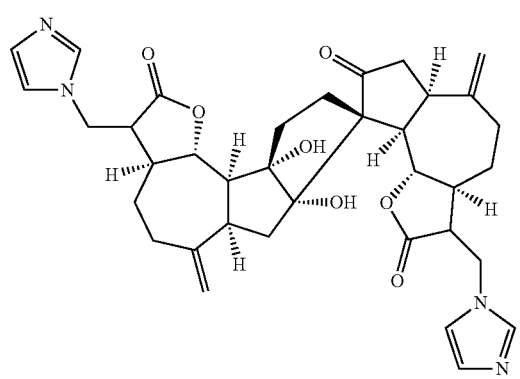

10. The compound of claim 1 wherein R1 is dimethylamine and R2 is H, of structure:

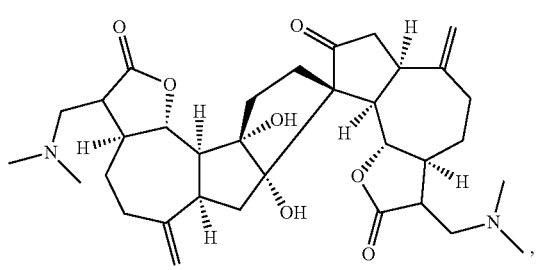

S1 or salt thereof.

11. The compound of claim 1 wherein R1 is dimethylamine and R2 is H, of structure:

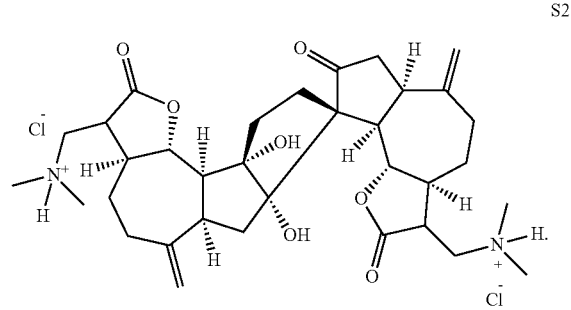

S2

12. A pharmaceutical composition comprising a compound of claim 1, wherein the salt is a pharmaceutically-acceptable salt, and a pharmaceutically-acceptable excipient, in unit dosage.

13. A pharmaceutical composition comprising:
(a) a compound of claim 1, or salt thereof, and
(b) a different anti-cancer medicament.

14. A pharmaceutical composition comprising:
(a) a compound of claim 1 or salt thereof, and
(b) a different anti-autoimmune or anti-inflammatory medicament.

15. A method of treating cancer related to aberrant activation of the nuclear factor-κβ (NF-κβ) signaling pathway comprising the step of administering to a person determined to be in need thereof a compound of claim 1, or salt thereof.

16. A synthetic method comprising steps (a) and (b):

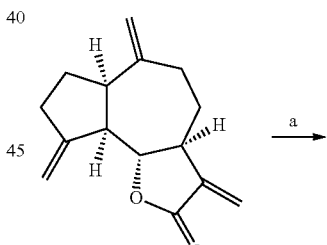

dehydrocostus lactone (6)

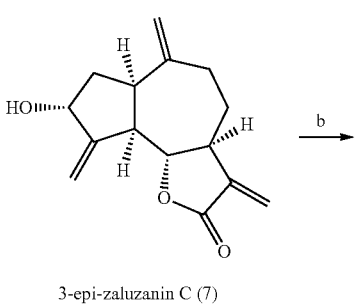

3-epi-zaluzanin C (7)

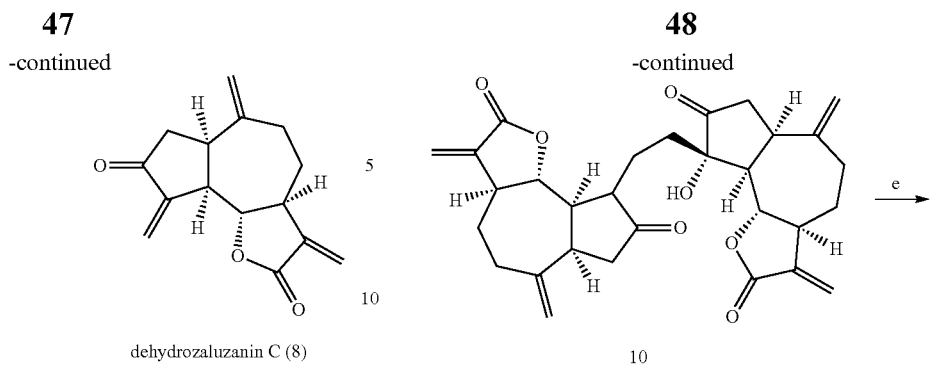

dehydrozaluzanin C (8)

(a) dehydrocostus lactone 6 is reacted with SeO$_2$ and t-BuOOH to form 3-epi-zaluzanin C 7;
(b) 3-epi-zaluzanin C 7 is reacted with Dess-Martin periodinane to form dehydrozaluzanin C 8.

17. The method of claim 16 further comprising subsequent steps (c), (d) and (e):

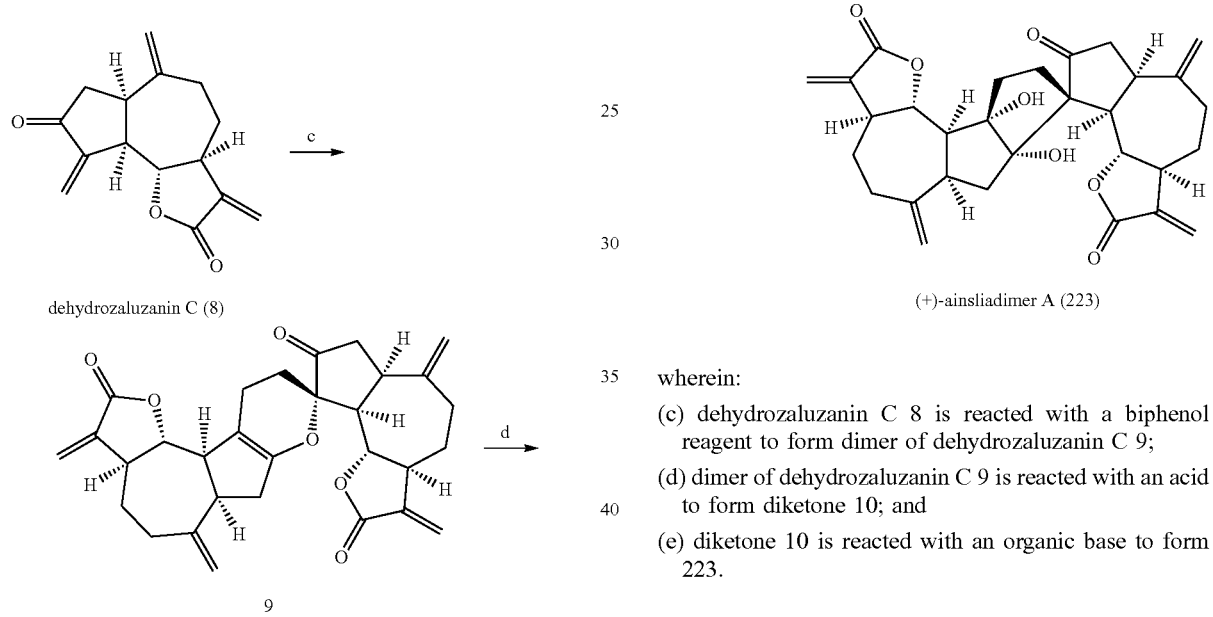

(+)-ainsliadimer A (223)

wherein:

(c) dehydrozaluzanin C 8 is reacted with a biphenol reagent to form dimer of dehydrozaluzanin C 9;
(d) dimer of dehydrozaluzanin C 9 is reacted with an acid to form diketone 10; and
(e) diketone 10 is reacted with an organic base to form 223.

* * * * *